United States Patent [19]
Jautelat et al.

[11] Patent Number: 6,057,353
[45] Date of Patent: May 2, 2000

[54] TRIAZOLYL-MERCAPTIDES AND THEIR USE AS MICROBICIDES

[75] Inventors: Manfred Jautelat, Burscheid; Stefan Dutzmann, Langenfeld; Klaus Stenzel, Düsseldorf, all of Germany

[73] Assignee: Bayer Aktiengesellschaft, Leverkusen, Germany

[21] Appl. No.: 09/171,733

[22] PCT Filed: Apr. 21, 1997

[86] PCT No.: PCT/EP97/01996

§ 371 Date: Oct. 23, 1998

§ 102(e) Date: Oct. 23, 1998

[87] PCT Pub. No.: WO97/41107

PCT Pub. Date: Nov. 6, 1997

[30] Foreign Application Priority Data

Apr. 30, 1996 [DE] Germany .................. 196 17 282

[51] Int. Cl.$^7$ .................. A01N 43/64; A01N 43/653; C07D 249/12; C07D 248/08
[52] U.S. Cl. .................. 514/384; 548/263.2; 548/264.4; 548/266.6; 548/267.2; 548/268.6
[58] Field of Search .................. 514/384; 548/263.2

[56] References Cited

U.S. PATENT DOCUMENTS

| | | | |
|---|---|---|---|
| 3,912,752 | 10/1975 | Meiser et al. | 260/308 R |
| 3,952,002 | 4/1976 | Kramer et al. | 260/308 R |
| 4,048,318 | 9/1977 | Meiser et al. | 424/269 |
| 4,079,062 | 3/1978 | Van Reet et al. | 260/308 R |
| 4,147,791 | 4/1979 | Meiser et al. | 424/269 |
| 4,205,075 | 5/1980 | Baldwin et al. | 424/269 |
| 4,243,405 | 1/1981 | Balasubramanyan et al. | 71/76 |
| 4,464,381 | 8/1984 | Janssen et al. | 424/269 |
| 4,532,341 | 7/1985 | Holmwood et al. | 549/559 |
| 4,549,900 | 10/1985 | Krämer et al. | 71/92 |
| 4,598,085 | 7/1986 | Heeres et al. | 514/383 |
| 4,626,595 | 12/1986 | Holmwood et al. | 549/559 |
| 4,652,580 | 3/1987 | Janssen et al. | 514/383 |
| 4,723,984 | 2/1988 | Holmwood et al. | 71/76 |
| 4,729,986 | 3/1988 | Olson | 514/63 |
| 4,789,672 | 12/1988 | Holmwood et al. | 514/184 |
| 4,871,390 | 10/1989 | Holmwood | 71/92 |
| 4,897,107 | 1/1990 | Holmwood et al. | 71/92 |
| 4,904,297 | 2/1990 | Kramer et al. | 71/92 |
| 4,904,298 | 2/1990 | Holmwood et al. | 71/92 |
| 4,906,652 | 3/1990 | Karbach et al. | 514/382 |
| 4,911,746 | 3/1990 | Holmwood et al. | 71/92 |
| 4,913,727 | 4/1990 | Stroech et al. | 71/92 |
| 4,952,232 | 8/1990 | Cuomo et al. | 71/92 |
| 4,965,280 | 10/1990 | Cuomo et al. | 514/383 |
| 4,965,281 | 10/1990 | Cuomo et al. | 514/399 |
| 4,968,712 | 11/1990 | Elbe et al. | 514/383 |
| 4,980,488 | 12/1990 | Stroech et al. | 549/563 |
| 4,988,819 | 1/1991 | Stroech et al. | 549/267.8 |
| 4,990,677 | 2/1991 | Stroech et al. | 568/29 |
| 5,034,052 | 7/1991 | Stroech et al. | 71/92 |
| 5,081,141 | 1/1992 | Colle et al. | 514/383 |
| 5,084,465 | 1/1992 | Cuomo et al. | 514/341 |
| 5,087,635 | 2/1992 | Shaber | 514/383 |
| 5,097,047 | 3/1992 | Stroech et al. | 549/463 |
| 5,256,683 | 10/1993 | Hutt et al. | 514/383 |
| 5,266,585 | 11/1993 | Hubele et al. | 514/383 |
| 5,308,743 | 5/1994 | Hutt et al. | 514/399 |
| 5,639,918 | 6/1997 | Hutt et al. | 568/329 |
| 5,789,430 | 8/1998 | Jautelat et al. | 514/272.4 |

FOREIGN PATENT DOCUMENTS

| | | |
|---|---|---|
| 0 015 756 | 9/1980 | European Pat. Off. . |
| 0 680 813 | 1/1983 | European Pat. Off. . |
| 0 069 442 | 2/1985 | European Pat. Off. . |
| 0 044 605 | 2/1986 | European Pat. Off. . |
| 0 061 835 | 2/1989 | European Pat. Off. . |
| 0 145 294 | 10/1989 | European Pat. Off. . |
| 0 267 778 | 3/1993 | European Pat. Off. . |
| 195 20 095 | 12/1996 | Germany . |
| 96/38423 | 12/1996 | WIPO . |
| 96/38424 | 12/1996 | WIPO . |
| 96/38440 | 12/1996 | WIPO . |
| 96/39395 | 12/1996 | WIPO . |
| 96/41798 | 12/1996 | WIPO . |
| 96/41804 | 12/1996 | WIPO . |
| 97/05119 | 2/1997 | WIPO . |
| 97/06151 | 2/1997 | WIPO . |
| 97/06152 | 2/1997 | WIPO . |

*Primary Examiner*—Johann Richter
*Assistant Examiner*—Jane C. Oswecki
*Attorney, Agent, or Firm*—Joseph C. Gil; Carol Marmo

[57] ABSTRACT

Triazoyl mercaptides of the formula (I)

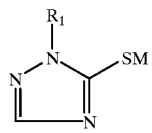

(I)

in which

M is an alkaline metal cation, an equivalent of an alkaline earth cation, an equivalent of a copper zinc, iron or nickel cation or an ammonium cation and $R^1$ is various radicals, a process for the production of the novel substances and their use to combat undesired microorganisms.

5 Claims, No Drawings

TRIAZOLYL-MERCAPTIDES AND THEIR USE AS MICROBICIDES

This application is a 371 of PCT/EP97/01996 filed Apr. 21, 1997.

The present invention relates to novel triazolyl-mercaptides, to a process for their preparation and to their use as microbicides.

It is already known that a large number of triazolyl derivatives have fungicidal properties (cf. EP-A 0 015 756, EP-A 0 040 345, EP-A 0 052 424, EP-A 0 061 835, EP-A 0 297 345, EP-A 0 094 564, EP-A 0 196 038, EP-A 0 267 778, EP-A 0 378 953, EP-A 0 068 813, EP-A 0 044 605, EP-A 0 069 442, EP-A 0 055 833, EP-A 0 301 393, DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786). The activity of these substances is good but, at low application rates, is not entirely satisfactory in some instances.

This invention, accordingly, provides novel triazolyl-mercaptides of the formula

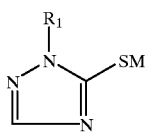

(I)

in which

M represents an alkali metal cation, an equivalent of an alkaline earth metal cation, an equivalent of a copper, zinc, iron or nickel cation or represents an ammonium cation of the formula

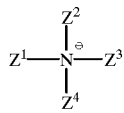

where $Z^1$ represents hydrogen or alkyl, $Z^2$ represents hydrogen or alkyl, $Z^3$ represents hydrogen, alkyl, benzyl or phenyl and $Z^4$ represents alkyl, benzyl or phenyl, and $R^1$ represents a radical of the formula

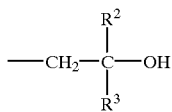

where $R^2$ and $R^3$ are identical or different and each represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, or $R^1$ represents a radical of the formula

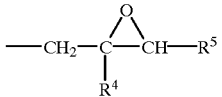

where $R^4$ represents alkyl having 1 to 4 carbon atoms, halogenoalkyl having 1 to 4 carbon atoms and 1 to 5 halogen atoms, optionally halogen-substituted cycloalkyl having 3 to 7 carbon atoms, naphthyl or phenyl which is optionally mono- to trisubstituted by identical or different substituents selected from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and/or halogenoalkylthio having 1 to 4 carbon atoms and 1 to 5 halogen atoms, and $R^5$ represents phenyl which is optionally mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and/or halogenoalkylthio having 1 to 4 carbon atoms and 1 to 5 halogen atoms, or $R^1$ represents a radical of the formula

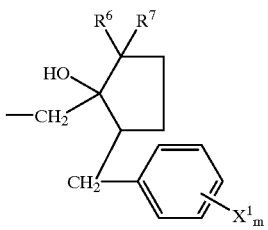

where $R^6$ and $R^7$ independently of one another each represent hydrogen or alkyl having 1 to 6 carbon atoms, $X^1$ represents halogen, alkyl having 1 to 5 carbon atoms, alkoxy having 1 to 4 carbon atoms, phenyl, phenoxy, halogenoalkyl having 1 to 4 carbon atoms and 1 to 5 halogen atoms, halogenoalkoxy having 1 to 4 carbon atoms and 1 to 5 halogen atoms or represents halogenoalkylthio having 1 to 4 carbon atoms and 1 to 5 halogen atoms, and m represents the numbers 0, 1 or 2, or $R^1$ represents a radical of the formula

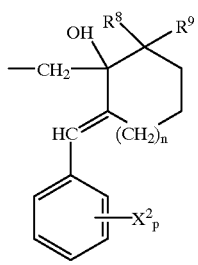

where $R^8$ and $R^9$ independently of one another each represent hydrogen or alkyl having 1 to 6 carbon atoms, $X^2$ represents halogen, cyano, nitro, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms or phenyl, n represents the numbers 0 or 1 and p represents the numbers 0, 1 or 2, or $R^1$ represents a radical of the formula

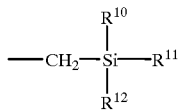

where $R^{10}$ represents alkyl having 2 to 18 carbon atoms, cycloalkyl having 3 to 6 carbon atoms, naphthyl or the radical of the formula

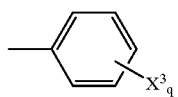

where $X^3$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and q represents the numbers 0, 1 or 2, $R^{11}$ and $R^{12}$ independently of one another each represent alkyl having 1 to 6 carbon atoms, alkoxy having 1 to 6 carbon atoms, cycloalkyl having 3 to 6 carbon atoms or represent the radical of the formula

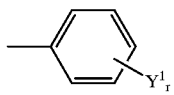

where $Y^1$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and r represents the numbers 0, 1 or 2, or $R^1$ represents a radical of the formula

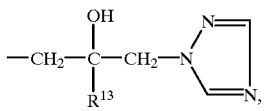

where $R^{13}$ represents alkyl having 1 to 6 carbon atoms, halogenoalkyl having 1 to 6 carbon atoms and 1 to 5 halogen atoms, cycloalkyl having 3 to 6 carbon atoms which is optionally substituted by halogen and/or alkyl having 1 to 4 carbon atoms, aryl which is optionally substituted or represents aralkyl which is optionally substituted, or $R^1$ represents a radical of the formula

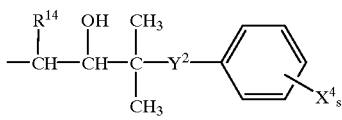

where $R^{14}$ represents hydrogen, alkyl or optionally substituted cycloalkyl, $X^4$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, s represents the numbers 0, 1, 2 or 3 and $Y^2$ represents an oxygen atom, a $CH_2$ group or a direct bond, or $R^1$ represents a radical of the formula

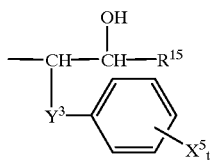

where
- $R^{15}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl,
- $X^5$ represents halogen, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms,
- t represents the numbers 0, 1, 2 or 3 and
- $Y^3$ represents an oxygen atom or represents a $CH_2$ group, or $R^1$ represents a radical of the formula

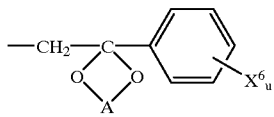

where
- A represents alkanediyl having 2 or 3 carbon atoms which is optionally substituted by halogen and/or alkyl having 1 to 4 carbon atoms,
- $X^6$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and
- u represents the numbers 0, 1, 2 or 3, or $R^1$ represents a radical of the formula

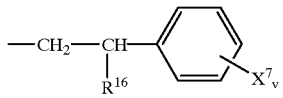

where
- $R^{16}$ represents alkyl having 1 to 10 carbon atoms, halogenoalkyl having 1 to 6 carbon atoms and 1 to 5 halogen atoms, fluoroalkoxyalkyl having 1 to 4 carbon atoms in the fluoroalkoxy moiety and 1 to 4 carbon atoms in the alkyl moiety, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents phenylalkyl having 1 to 4 carbon atoms in the alkyl moiety which is optionally substituted by halogen,
- $X^7$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, and
- v represents the numbers 0, 1, 2 or 3, or $R^1$ represents a radical of the formula

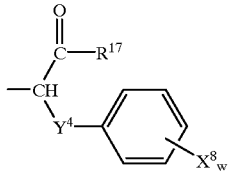

where
- $R^{17}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl,
- $X^8$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms,
- w represents the numbers 0, 1, 2 or 3 and
- $Y^4$ represents an oxygen atom or represents a $CH_2$ group, or $R^1$ represents a radical of the formula

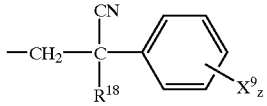

where
- $R^{18}$ represents alkyl having 1 to 6 carbon atoms, halogenoalkyl having 1 to 6 carbon atoms and 1 to 5 halogen atoms, optionally substituted aryl or represents optionally substituted aralkyl, $X^9$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and z represents the numbers 0, 1, 2 or 3.

A large number of the substances according to the invention contain one or more asymmetrically substituted carbon atoms. They can therefore be obtained in the form of optical isomers. The present invention relates both to the individual isomers and to mixtures thereof.

Furthermore, it has been found that triazolyl-mercaptides of the formula (I) are obtained when mercapto-triazoles of the formula

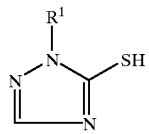

(II)

in which $R^1$ is as defined above, are either a) reacted with hydroxides of the formula

 (III)

in which $M^1$ represents an alkali metal cation, an equivalent of an alkaline earth metal cation or represents an ammonium cation of the formula

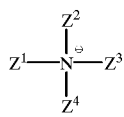

in which $Z^1$, $Z^2$, $Z^3$ and $Z^4$ are each as defined above, in the presence of a diluent, or b) reacted with amines of the formula

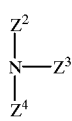

(IV)

in which $Z^2$, $Z^3$ and $Z^4$ are each as defined above, in the presence of a diluent, or c) reacted with acetates of the formula

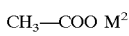 (V)

in which $M^2$ represents an equivalent of a copper, zinc, iron or nickel cation, in the presence of a diluent.

Finally, it has been found that the novel triazolyl-mercaptides of the formula (I) have very good microbicidal properties and can be used both in crop protection and in the protection of materials for controlling undesirable microorganisms.

Surprisingly, the substances according to the invention have better fungicidal activity, in particular fungicidal activity, than the constitutionally most similar compounds of the same direction of action.

The formula (I) provides a general definition of the triazolyl-mercaptides according to the invention.

M preferably represents a lithium, sodium or potassium cation, an equivalent of a magnesium, calcium, copper, zinc, iron or nickel cation or represents an ammonium cation of the formula

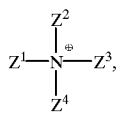

in which $Z^1$ preferably represents hydrogen or straight-chain or branched alkyl having 1 to 8carbon atoms, $Z^2$ preferably represents hydrogen or straight-chain or branched alkyl having 1 to 8 carbon atoms, $Z^3$ preferably represents hydrogen, straight-chain or branched alkyl having 1 to 8 carbon atoms, benzyl or phenyl and $Z^4$ preferably represents straight-chain or branched alkyl having 1 to 18 carbon atoms, benzyl or phenyl.

$R^1$ preferably represents a radical of the formula

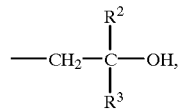

in which $R^2$ preferably represents straight-chain or branched alkyl having 1 to 6 carbon atoms, where these radicals may be mono- to tetrasubstituted by identical or different substituents selected from the group consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, where each of these radicals may be mono- to trisubstituted by identical or different substituents selected from the group consisting of halogen, alkoxy having 1 to 4 carbon atoms and/or cycloalkyl having 3 to 7 carbon atoms, or represents cycloalkyl having 3 to 7 carbon atoms, where each of these radicals may be mono- to trisubstituted by identical or different substituents selected from the group consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, where each of these radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused five- or six-membered heteroaromatic radical having 1 to 3 hetero atoms, such as nitrogen, sulphur and/or oxygen, where each of these radicals may be mono- to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano, and $R^3$ preferably represents straight-chain or branched alkyl having 1 to 6 carbon atoms, where these radicals may be mono- to tetrasubstituted by identical or different substituents selected from the group consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, where each of these radicals may be mono- to trisubstituted by identical or different substituents selected from the group consisting of halogen, alkoxy having 1 to 4 carbon atoms and/or cycloalkyl having 3 to 7 carbon atoms, or represents cycloalkyl having 3 to 7 carbon atoms, where each of these radicals may be mono- to trisubstituted by identical or different substituents selected from the group consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, where each of these radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused five- or six-membered heteroaromatic radical having 1 to 3 hetero atoms, such as nitrogen, sulphur and/or oxygen, where each of these radicals may be mono- to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano.

$R^1$ furthermore preferably represents a radical of the formula

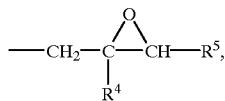

in which $R^4$ preferably represents methyl, ethyl, n-propyl, isopropyl, n-butyl, sec-butyl, isobutyl, tert-butyl, fluoro-tert-butyl, difluoro-tert-butyl, cycloalkyl having 3 to 6 carbon atoms which is optionally mono- to trisubstituted by identical or different substituents selected from the group consisting of fluorine, chlorine and/or bromine, represents naphthyl or represents phenyl which may be mono- to trisubstituted by identical or different substituents selected from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and/or trifluoromethylthio, and $R^5$ preferably represents phenyl which may be mono- to trisubstituted by identical or different substituents selected from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and/or trifluoromethylthio.

$R^1$ furthermore preferably represents a radical of the formula

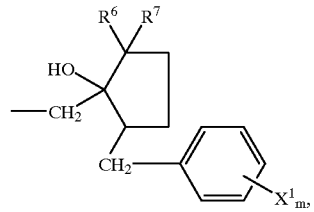

in which $R^6$ preferably represents hydrogen, methyl, ethyl, n-propyl, isopropyl, n-butyl, isobutyl, sec-butyl, tert-butyl or n-pentyl, $R^7$ preferably represents hydrogen, methyl, ethyl, n-propyl, isopropyl, n-butyl, isobutyl, sec-butyl, tert-butyl or n-pentyl, $X^1$ preferably represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m also preferably represents the numbers 0, 1 or 2, where $X^1$ may represent identical or different radicals if m represents 2.

$R^1$ furthermore preferably represents a radical of the formula

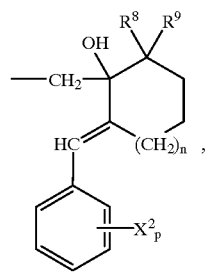

in which $R^8$ preferably represents hydrogen, methyl, ethyl, n-propyl, isopropyl, n-butyl, isobutyl, sec-butyl, tert-butyl or n-pentyl, $R^9$ preferably represents hydrogen, methyl, ethyl, n-propyl, isopropyl, n-butyl, isobutyl, sec-butyl, tert-butyl or n-pentyl, $X^2$ preferably represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also preferably represents the numbers 0 or 1 and p also preferably represents the numbers 0, 1 or 2, where $X^2$ may represent identical or different radicals if p represents 2.

$R^1$ furthermore preferably represents a radical of the formula

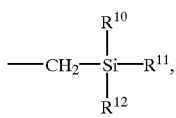

where $R^{10}$ preferably represents alkyl having 2 to 12 carbon atoms, cycloalkyl having 5 or 6 carbon atoms or represents the radical of the formula

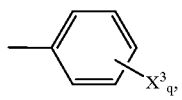

where $X^3$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and q also preferably represents the numbers 0, 1 or 2, where $X^3$ represents identical or different radicals if q represents 2, $R^{11}$ preferably represents alkyl having 1 to 4 carbon atoms or represents the radical of the formula

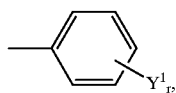

where $Y^1$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and r also preferably represents the numbers 0, 1 or 2, where $Y^1$ represents identical or different radicals if r represents 2, and $R^{12}$ preferably represents alkyl having 1 to 4 carbon atoms.

$R^1$ furthermore preferably represents a radical of the formula

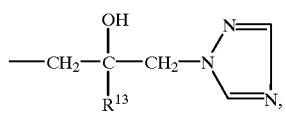

in which $R^{13}$ preferably represents straight-chain or branched alkyl having 1 to 4 carbon atoms, straight-chain or branched halogenoalkyl having 1 to 4 carbon atoms and 1 to 5 fluorine, chlorine and/or bromine atoms, represents cycloalkyl having 3 to 6 carbon atoms which is optionally mono- to trisubstituted by identical or different substituents selected from the group consisting of fluorine, chlorine, bromine, methyl and/or ethyl, represents phenyl, benzyl or phenethyl, where each of the three last-mentioned radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or phenoxy which is optionally substituted by halogen and/or alkyl having 1 to 4 carbon atoms.

$R^1$ furthermore preferably represents a radical of the formula

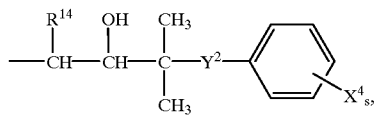

in which $R^{14}$ preferably represents hydrogen, straight-chain or branched alkyl having 1 to 12 carbon atoms or represents cycloalkyl having 3 to 7 carbon atoms which is optionally mono- to trisubstituted by identical or different substituents selected from the group consisting of halogen and/or alkyl having 1 to 4 carbon atoms, $X^4$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy, s preferably represents the numbers 0, 1, 2 or 3, where $X^4$ represents identical or different radicals if s represents 2 or 3, and $Y^2$ preferably represents an oxygen atom, a $CH_2$ group or a direct bond.

$R^1$ furthermore preferably represents a radical of the formula

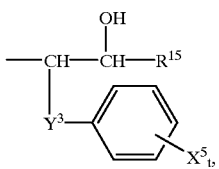

in which
R[15] preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and/or bromine or represents benzyl which is optionally mono- to trisubstituted by identical or different substituents selected from the group consisting of fluorine, chlorine and/or bromine, $X^5$ preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl which is optionally mono- to disubstituted by identical or different substituents selected from the group consisting of fluorine, chlorine, bromine and/or methyl or represents phenoxy which is optionally mono- to disubstituted by identical or different substituents selected from the group consisting of fluorine, chlorine, bromine and/or methyl, t preferably represents the numbers 0, 1, 2 or 3, where $X^5$ represents identical or different radicals if t represents 2 or 3 and $Y^3$ also preferably represents an oxygen atom or represents a $CH_2$ group.

$R^1$ furthermore preferably represents a radical of the formula

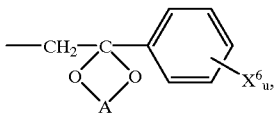

in which
A preferably represents alkanediyl having 2 or 3 carbon atoms which is optionally mono- to trisubstituted by identical or different substituents selected from the group consisting of fluorine, chlorine, bromine, methyl, ethyl, n-propyl, isopropyl, n-butyl, i-butyl, sec-butyl and/or tert-butyl, $X^6$ preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents selected from the group consisting of fluorine, chlorine and/or methyl and/or represents phenoxy which is optionally mono- to trisubstituted by identical or different substituents selected from the group consisting of fluorine, chlorine and/or methyl and u preferably represents the numbers 0, 1, 2 or 3, where $X^6$ represents identical or different radicals if u represents 2 or 3.

$R^1$ furthermore preferably represents a radical of the formula

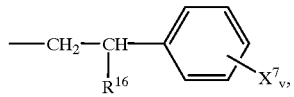

in which
R[16] preferably represents straight-chain or branched alkyl having 1 to 6 carbon atoms, straight-chain or branched halogenoalkyl having 1 to 6 carbon atoms and 1 to 5 fluorine, chlorine and/or bromine atoms, fluoroalkoxyalkyl having 1 to 3 carbon atoms and 1 to 5 fluorine atoms in the fluoroalkoxy moiety and 1 to 3 carbon atoms in the alkyl moiety, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and/or bromine or represents phenylalkyl having 1 or 2 carbon atoms in the alkyl moiety which is optionally mono- to trisubstituted by identical or different substituents selected from the group consisting of fluorine, chlorine and/or bromine, $X^7$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl and v preferably represents the numbers 0, 1, 2 or 3, where $X^7$ represents identical or different radicals if v represents 2 or 3.

$R^1$ furthermore preferably represents a radical of the formula

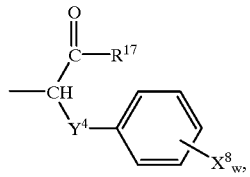

in which
R[17] preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and/or bromine or represents benzyl which is optionally mono- to trisubstituted by identical or different substituents selected from the group consisting of fluorine, chlorine and/or bromine, $X^8$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl, w preferably represents the numbers 0, 1, 2 or 3, where $X^8$ represents identical or different radicals if w represents 2 or 3, and $Y^4$ preferably represents an oxygen atom or represents a $CH_2$ group.

$R^1$ furthermore preferably represents a radical of the formula

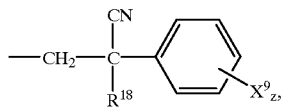

in which $R^{18}$ preferably represents straight-chain or branched alkyl having 1 to 4 carbon atoms, halogenoalkyl having 1 to 4 carbon atoms and 1 to 5 halogen atoms, phenyl which is optionally mono- to trisubstituted by identical or different substituents selected from the group consisting of halogen, alkyl having 1 to 4 carbon atoms, halogenoalkyl having 1 or 2 carbon atoms having 1 to 5 halogen atoms, alkoxy having 1 to 4 carbon atoms and/or halogenoalkoxy having 1 or 2 carbon atoms and 1 to 5 halogen atoms or represents phenylalkyl having 1 to 4 carbon atoms in the alkyl moiety which is optionally mono- to trisubstituted by identical or different substituents selected from the group consisting of halogen, alkyl having 1 to 4 carbon atoms, halogenoalkyl having 1 or 2 carbon atoms and 1 to 5 halogen atoms, alkoxy having 1 to 4 carbon atoms and/or halogenoalkoxy having 1 or 2 carbon atoms and 1 to 5 halogen atoms, $X^9$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl, and z preferably represents the numbers 0, 1, 2 or 3, where $X^9$ represents identical or different radicals if z represents 2 or 3.

M particularly preferably represents a lithium, sodium or potassium cation, an equivalent of a magnesium, calcium, copper, zinc, iron or nickel cation or represents an ammonium cation of the formula

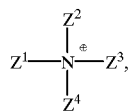

in which $Z^1$ particularly preferably represents hydrogen or straight-chain or branched alkyl having 1 to 6 carbon atoms, $Z^2$ particularly preferably represents hydrogen or straight-chain or branched alkyl having 1 to 6 carbon atoms, $Z^3$ particularly preferably represents hydrogen, straight-chain or branched alkyl having 1 to 6 carbon atoms, benzyl or phenyl and $Z^4$ particularly preferably represents straight-chain or branched alkyl having 1 to 18 carbon atoms, benzyl or phenyl.

$R^1$ particularly preferably represents a radical of the formula

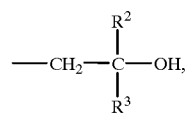

in which $R^2$ particularly preferably represents straight-chain or branched alkyl having 1 to 4 carbon atoms, where these radicals may be mono- to tetrasubstituted by identical or different substituents selected from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, where each of these radicals may be mono- to trisubstituted by identical or different substituents selected from the group consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, where each of these radicals may be mono- to trisubstituted by identical or different substituents selected from the group consisting of fluorine, chlorine, bromine, cyano, methyl, ethyl, propyl, isopropyl and/or tert-butyl, or represents phenylalkyl having 1 to 4 carbon atoms in the straight-chain or branched alkyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenylalkenyl having 2 to 4 carbon atoms in the alkenyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenoxyalkyl having 1 to 4 carbon atoms in the straight-chain or branched oxyalkyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenyl which may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl, and $R^3$ particularly preferably represents straight-chain or branched alkyl having 1 to 4 carbon atoms, where these radicals may be mono- to tetrasubstituted by identical or different substituents selected from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, where each of these radicals may be mono- to trisubstituted by identical or different substituents selected from the group consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, where each of these radicals may be mono- to trisubstituted by identical or different substituents selected from the group consisting of fluorine, chlorine, bromine, cyano, methyl, ethyl, propyl, isopropyl and/or tert-butyl, or represents phenylalkyl having 1 to 4 carbon atoms in the straight-chain or branched alkyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenylalkenyl having 2 to 4 carbon atoms in the alkenyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenoxyalkyl having 1 to 4 carbon atoms in the straight-chain or branched oxyalkyl moiety, where the phenyl moiety may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenyl which may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl.

$R^1$ furthermore particularly preferably represents a radical of the formula

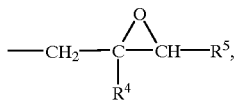

in which

R⁴ particularly preferably represents methyl, ethyl, n-propyl, isopropyl, n-butyl, sec-butyl, isobutyl, tert-butyl, fluoro-tert-butyl, difluoro-tert-butyl, cycloalkyl having 3 to 6 carbon atoms which is optionally mono- to trisubstituted by identical or different substituents selected from the group consisting of fluorine, chlorine and/or bromine, represents naphthyl or represents phenyl which may be mono- to trisubstituted by identical or different substituents selected from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and/or trifluoromethylthio, and R⁵ particularly preferably represents phenyl which may be mono- to trisubstituted by identical or different substituents selected from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and/or trifluoromethylthio.

$R^1$ furthermore particularly preferably represents a radical of the formula

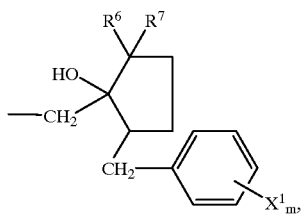

in which $R^6$ particularly preferably represents hydrogen, methyl, ethyl, n-propyl, isopropyl, n-butyl, isobutyl, sec-butyl, tert-butyl or n-pentyl, $R^7$ particularly preferably represents hydrogen, methyl, ethyl, n-propyl, isopropyl, n-butyl, isobutyl, sec-butyl, tert-butyl or n-pentyl, $X^1$ particularly preferably represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m also particularly preferably represents the numbers 0, 1 or 2,
   where $X^1$ may represent identical or different radicals if mn represents 2.

$R^1$ furthermore particularly preferably represents a radical of the formula

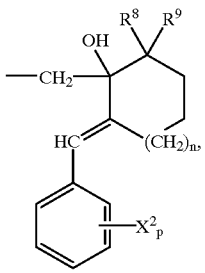

in which $R^8$ particularly preferably represents hydrogen, methyl, ethyl, n-propyl, isopropyl, n-butyl, isobutyl, sec-butyl, tert-butyl or n-pentyl, $R^9$ particularly preferably represents hydrogen, methyl, ethyl, n-propyl, isopropyl, n-butyl, isobutyl, sec-butyl, tert-butyl or n-pentyl, $X^2$ particularly preferably represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also particularly preferably represents the numbers 0 or 1 and p also particularly preferably represents the numbers, 0, 1 or 2,
   where $X^2$ may represent identical or different radicals if p represents 2.

$R^1$ furthermore particularly preferably represents a radical of the formula

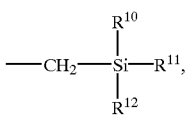

where $R^{10}$ particularly preferably represents the radical of the formula

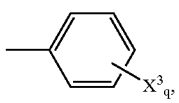

where $X^3$ particularly preferably represents fluorine, chlorine, bromine, methyl, methoxy, methylthio, trichloromethyl, trifluoromethyl, trifluoromethoxy, difluoromethoxy or phenyl and q also particularly preferably represents the numbers 0, 1 or 2, where $X^3$ represents identical or different radicals if q represents 2, $R^{11}$ particularly preferably represents methyl, ethyl, n-propyl, n-butyl or represents the radical of the formula

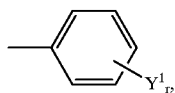

where
- $Y^1$ particularly preferably represents fluorine, chlorine, bromine, methyl, ethyl, methoxy, trichloromethyl, trifluoromethyl, trifluoromethoxy, difluoromethoxy or phenyl, and
- r also particularly preferably represents the numbers 0, 1 or 2, where $Y^1$ represents identical or different radicals if r represents 2, and
- $R^{12}$ particularly preferably represents methyl, ethyl, n-propyl or n-butyl.

$R^1$ furthermore particularly preferably represents a radical of the formula

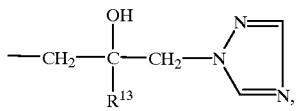

in which
- $R^{13}$ particularly preferably represents methyl, ethyl, n-propyl, isopropyl, n-butyl, sec-butyl, isobutyl, tert-butyl, halogenoalkyl having 1 to 4 carbon atoms and 1 to 3 fluorine, chlorine and/or bromine atoms, cyclopropyl, cyclopentyl or cyclohexyl which is optionally mono- to trisubstituted by identical or different substituents selected from the group consisting of fluorine, chlorine, bromine, methyl and/or ethyl, and represents phenyl, benzyl or phenethyl, where each of the three last-mentioned radicals may be mono- to trisubstituted in the phenyl moiety by identical or different substituents selected from the group consisting of fluorine, chlorine, bromine, methyl, ethyl, methoxy, methylthio, trichloromethyl, trifluoromethyl, trifluoromethoxy, difluoromethoxy, trifluoromethylthio, phenyl and/or phenoxy.

$R^1$ furthermore particularly preferably represents a radical of the formula

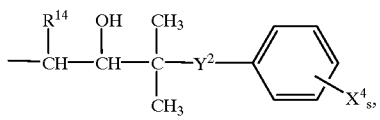

in which
- $R^{14}$ particularly preferably represents hydrogen, straight-chain or branched alkyl having 1 to 6 carbon atoms or represents cyclopropyl, cyclopentyl or cyclohexyl which is optionally mono- to trisubstituted by identical or different substituents selected from the group consisting of fluorine, chlorine, bromine, methyl and/or ethyl,
- $X^4$ particularly preferably represents fluorine, chlorine, bromine, methyl, methoxy, methylthio, trichloromethyl, trifluoromethyl, trifluoromethoxy, difluoromethoxy, trifluoromethylthio, phenyl or phenoxy,
- s also particularly preferably represents the numbers 0, 1, 2 or 3, where $X^4$ represents identical or different radicals if s represents 2 or 3 and
- $Y^2$ also particularly preferably represents an oxygen atom, a $CH_2$ group or a direct bond.

$R^1$ furthermore particularly preferably represents a radical of the formula

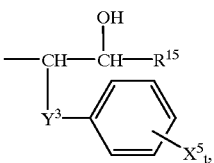

in which
- $R^{15}$ particularly preferably represents methyl, isopropyl, tert-butyl, fluoro-tert-butyl, difluoro-tert-butyl, cyclopropyl, cyclopentyl or cyclohexyl which is optionally mono- to trisubstituted by identical or different substituents selected from the group consisting of fluorine, chlorine and/or methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents selected from the group consisting of fluorine, chlorine and/or bromine or represents benzyl which is optionally mono- or disubstituted by identical or different substituents selected from the group consisting of fluorine, chlorine and/or bromine,
- $X^5$ particularly preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl or phenoxy,
- t also particularly preferably represents the numbers 0, 1, 2 or 3, where $X^5$ represents identical or different radicals if t represents 2 or 3 and
- $Y^3$ also particularly preferably represents an oxygen atom or represents a $CH_2$ group.

$R^1$ furthermore particularly preferably represents a radical of the formula

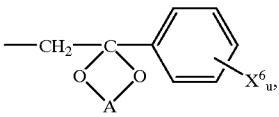

in which
- A particularly preferably represents alkanediyl having 2 or 3 carbon atoms which is optionally mono- to trisubstituted by identical or different substituents selected from the group consisting of fluorine, chlorine, bromine, methyl, ethyl, n-propyl, isopropyl, n-butyl, i-butyl, sec-butyl and/or tert-butyl,
- $X^6$ particularly preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents selected from the group consisting of fluorine, chlorine and/or methyl and/or represents phenoxy which is optionally mono- to trisubstituted by identical or different substituents selected from the group consisting of fluorine, chlorine and/or methyl and u also particularly preferably represents the numbers 0, 1, 2 or 3, where $X^6$ represents identical or different radicals if u represents 2 or 3.

$R^1$ furthermore particularly preferably represents a radical of the formula

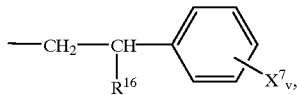

in which $R^{16}$ particularly preferably represents methyl, ethyl, n-propyl, isopropyl, n-butyl, isobutyl, sec-butyl, tert-butyl, halogenoalkyl having 1 to 4 carbon atoms and 1 to 5 fluorine, chlorine and/or bromine atoms, fluoroalkoxyalkyl having 1 or 2 carbon atoms and 1 to 5 fluorine atoms in the fluoroalkoxy moiety and 1 or 2 carbon atoms in the alkyl moiety, cyclopropyl, cyclopentyl or cyclohexyl which is optionally mono- to trisubstituted by identical or different substituents selected from the group consisting of fluorine, chlorine, and/or methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents selected from the group consisting of fluorine, chlorine and/or bromine or represents benzyl which is optionally mono- or disubstituted by identical or different substituents selected from the group consisting of fluorine, chlorine and/or bromine, $X^7$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy and v also particularly preferably represents the numbers 0, 1, 2 or 3, where $X^7$ represents identical or different radicals if v represents 2 or 3.

$R^1$ furthermore particularly preferably represents a radical of the formula

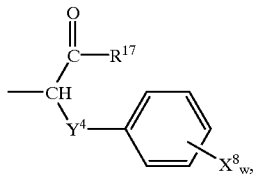

in which $R^{17}$ particularly preferably represents methyl, isopropyl, tert-butyl, fluoro-tert-butyl, difluoro-tert-butyl, cyclopropyl, cyclopentyl or cyclohexyl which is optionally mono- to trisubstituted by identical or different substituents selected from the group consisting of fluorine, chlorine, and/or methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents selected from the group consisting of fluorine, chlorine and/or bromine or represents benzyl which is optionally mono- or disubstituted by identical or different substituents selected from the group consisting of fluorine, chlorine and/or bromine, $X^8$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, $Y^4$ also particularly preferably represents an oxygen atom or represents a $CH_2$ group, and w also particularly preferably represents the numbers 0, 1, 2 or 3, where $X^8$ represents identical or different radicals if w represents.

$R^1$ furthermore also preferably represents a radical of the formula

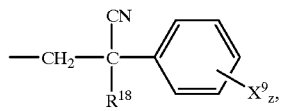

in which $R^{18}$ particularly preferably represents methyl, ethyl, n-propyl, isopropyl, n-butyl, sec-butyl, isobutyl, tert-butyl, fluoro-tert-butyl, difluoro-tert-butyl, phenyl which is optionally mono- or disubstituted by identical or different substituents selected from the group consisting of fluorine, chlorine, methyl, ethyl, trifluoromethyl, trichloromethyl, methoxy, ethoxy, trifluoromethoxy and/or difluoromethoxy or represents phenylalkyl having 1 or 2 carbon atoms in the alkyl moiety which is optionally mono- or disubstituted in the phenyl moiety by identical or different substituents selected from the group consisting of fluorine, chlorine, bromine, methyl, ethyl, trifluomethyl, trichloromethyl, methoxy, ethoxy, trifluoromethoxy and/or difluoromethoxy, $X^9$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, and z also particularly preferably represents the numbers 0, 1, 2 or 3, where $X^9$ represents identical or different radicals if z represents 2 or 3.

The mercapto-triazoles required as starting materials in the preparation of the substances according to the invention can be present in the "mercapto" form of the formula (II)

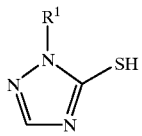

or in the tautomeric "thiono" form of the formula

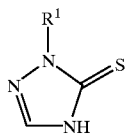
(IIa)

Therefore, it cannot be excluded that some or all of the substances according to the invention are derived from the "thiono" form of the formula (IIa). This means, that the substances according to the invention are present either as substances of the formula

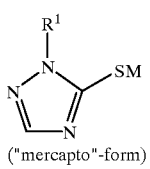
(I)
("mercapto"-form)

or of the formula

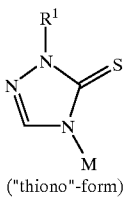
(Ia)
("thiono"-form)

or have a mesomeric structure of the formula

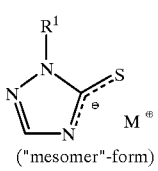
(I')
("mesomer"-form)

For simplicity, only the "mercapto" form is given in each case.

Examples of substances according to the invention include the triazolyl-mercaptides listed in the tables below.

TABLE 1

Ib $$R^2-\underset{\underset{CH_2}{|}}{\underset{|}{\overset{OH}{\overset{|}{C}}}}-R^3$$

[triazole ring with $S^{\ominus}M^{\oplus}$]

| $R^2$ | $R^3$ | M |
|---|---|---|
| Cl—C₆H₄—CH₂—CH₂— | —C(CH₃)₃ | Na |
| Cl—C₆H₄—CH₂—CH₂— | —C(CH₃)₃ | ½ Cu |
| Cl—C₆H₄—CH₂—CH₂— | —C(CH₃)₃ | H(C₂H₅)₃ |
| Cl—C₆H₄—CH₂—CH₂— | —C(CH₃)₃ | N(CH₃)₄ |
| Cl—C₆H₄—CH₂—CH₂— | —C(CH₃)₃ | ⅓ Fe |

TABLE 1-continued
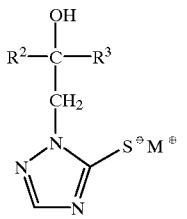
| R² | R³ | M |
|---|---|---|
| 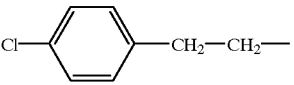 | —C(CH₃)₃ | H₃N-C₁₈H₃₇ |
| 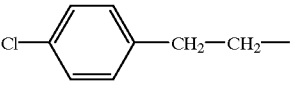 | —C(CH₃)₃ | H₂N(iC₃H₇)₂ |
| 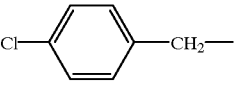 | —C(CH₃)₃ | Na |
| 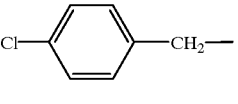 | —C(CH₃)₃ | K |
| 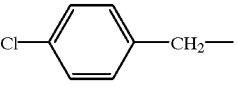 | —C(CH₃)₃ | ½ Ca |
| 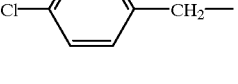 | —C(CH₃)₃ | ½ Ni |
| 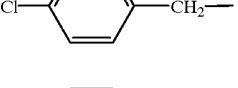 | —C(CH₃)₃ | HN(C₂H₅)₃ |
| 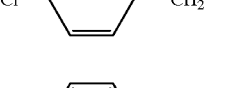 | —C(CH₃)₃ | N(CH₃)₄ |
| 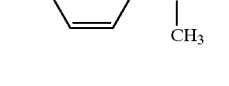 | —C(CH₃)₃ | Na |
| 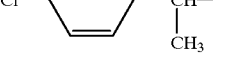 | —C(CH₃)₃ | HN(C₂H₅)₃ |
| 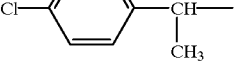 | —C(CH₃)₃ | HN(C₄H₉-n)₃ |

TABLE 1-continued
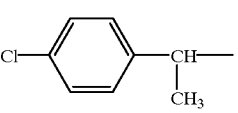
| R² | R³ | M |
|---|---|---|
| 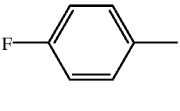 | —C(CH₃)₃ | ½ Zn |
| 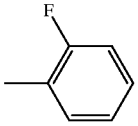 | 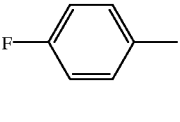 | Na |
| 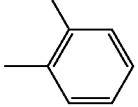 | 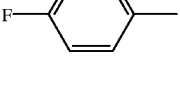 | ½ Cu |
| 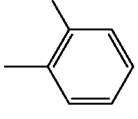 | 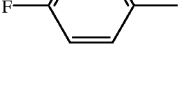 | HN(C₂H₅)₃ |
| 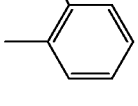 | 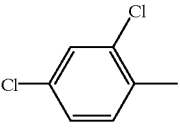 | N(CH₃)₄ |
| 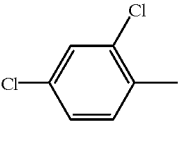 | —C₄H₉-n | Na |
| 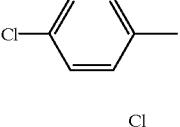 | —C₄H₉-n | ½ Cu |
| 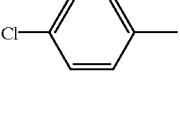 | —C₄H₉-n | K |
| 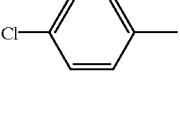 | —C₄H₉-n | HN(C₂H₅)₃ |

TABLE 1-continued

Structure Ib:

R²−C(OH)(R³)−CH₂−N(triazole)−S⁻ M⁺

(1-substituted-1,2,4-triazole with S⁻M⁺ at position 5, and CH₂−C(OH)(R²)(R³) at N1)

| R² | R³ | M |
|---|---|---|
| 4-Cl-C₆H₄− | −CH(CH₃)(cyclopropyl) | Na |
| 4-Cl-C₆H₄− | −CH(CH₃)(cyclopropyl) | ½ Cu |
| 4-Cl-C₆H₄− | −CH(CH₃)(cyclopropyl) | HN(C₂H₅)₃ |
| 4-Cl-C₆H₄− | −CH(CH₃)(cyclopropyl) | N(CH₃)₄ |
| 4-Cl-C₆H₄−O−CH₂− | −C(CH₃)₃ | Na |
| 4-Cl-C₆H₄−O−CH₂− | −C(CH₃)₃ | ½ Cu |
| 4-Cl-C₆H₄−O−CH₂− | −C(CH₃)₃ | HN(C₂H₅)₃ |
| 4-Cl-C₆H₄−O−CH₂− | −C(CH₃)₃ | H₂N(iC₃H₇)₂ |
| Cl₂CH−CCl₂−CH₂− | −C(CH₃)₃ | Na |
| Cl₂CH−CCl₂−CH₂− | −C(CH₃)₃ | ½ Cu |
| Cl₂CH−CCl₂−CH₂− | cyclopropyl-Cl | Na |
| Cl₂CH−CCl₂−CH₂− | cyclopropyl-Cl | HN(C₂H₅)₃ |
| Cl₂CH−CCl₂−CH₂− | cyclopropyl-F | Na |
| Cl₂CH−CCl₂−CH₂− | cyclopropyl-F | ½ Cu |

TABLE 1-continued
Ib
| R² | R³ | M |
|---|---|---|
| Cl₂C=CCl-CH₂— | 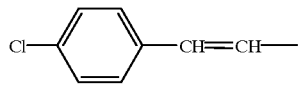 | Na |
| 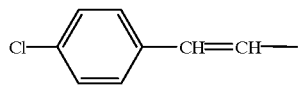 | —C(CH₃)₃ | Na |
| 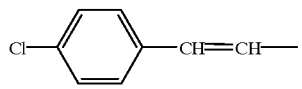 | —C(CH₃)₃ | ½ Cu |
|  | 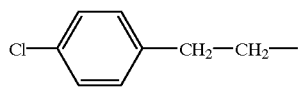 | Na |
|  | 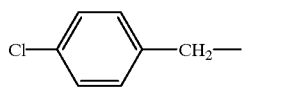 | Na |
|  | 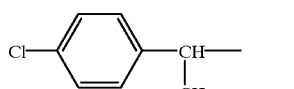 | Na |
|  | 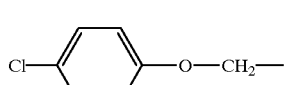 | Na |
|  | 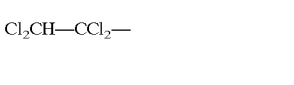 | Na |
| Cl₂CH—CCl₂— |  | Na |
| 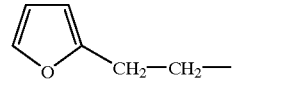 | —C(CH₃)₃ | Na |
| 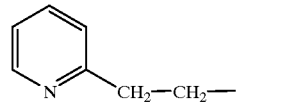 | —C(CH₃)₃ | Na |
| 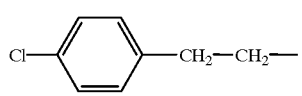 | —C(CH₃)₃ | ½ Mg |

TABLE 2
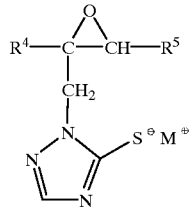
(Ic)
| R⁴ | R⁵ | M |
|---|---|---|
| 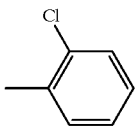 | 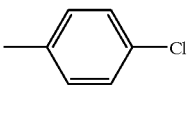 | Na |
| 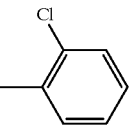 | 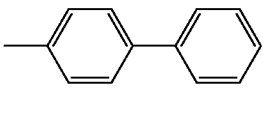 | Na |
| 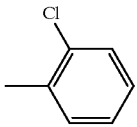 | 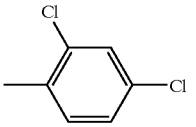 | Na |
| 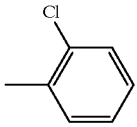 | 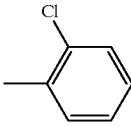 | Na |
| 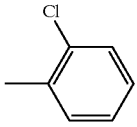 | 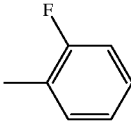 | Na |
| 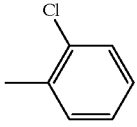 | 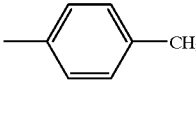 | Na |
| 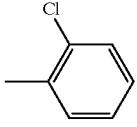 | 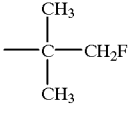 | Na |
| 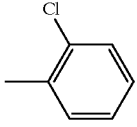 |  | Na |

TABLE 2-continued
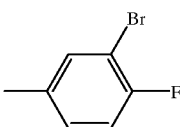
(Ic)
| R⁴ | R⁵ | M |
|---|---|---|
| 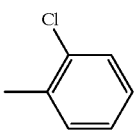 | 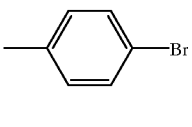 | Na |
| 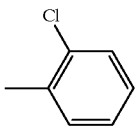 | 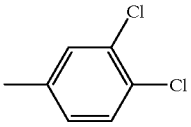 | Na |
| 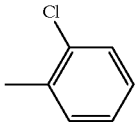 | 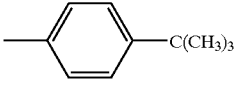 | Na |
| 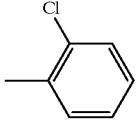 | 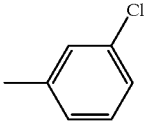 | Na |
| 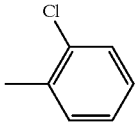 | 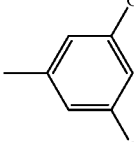 | Na |
| 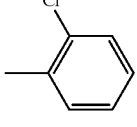 | 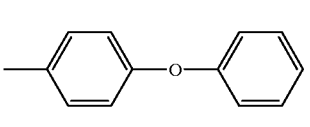 | Na |
| 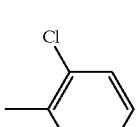 | 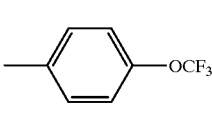 | Na |
| 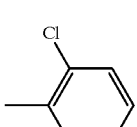 | | Na |

TABLE 2-continued (Ic)

| R⁴ | R⁵ | M |
|---|---|---|
| 4-(SCF₃)-phenyl | 2-Cl-phenyl | Na |
| 4-F-phenyl | 2-(OCHF₂)-phenyl | Na |
| 4-Cl-phenyl | 2-F-phenyl | Na |
| 4-biphenyl | 2-F-phenyl | Na |
| phenyl | 2-F-phenyl | Na |
| 2,4-diCl-phenyl | 2-F-phenyl | Na |
| 2-Cl-phenyl | 2-F-phenyl | Na |
| 2-F-phenyl | 2-F-phenyl | Na |

TABLE 2-continued
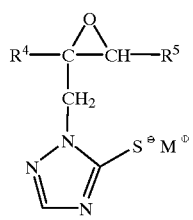
(Ic)
| R⁴ | R⁵ | M |
|---|---|---|
| 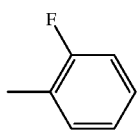 | 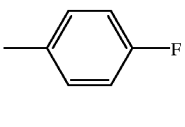 | Na |
| 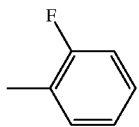 | 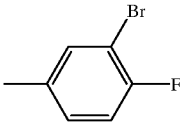 | Na |
| 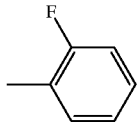 | 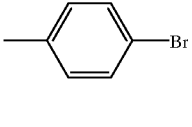 | Na |
| 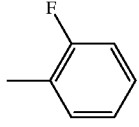 | 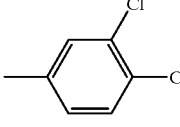 | Na |
| 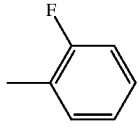 | 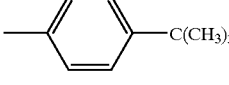 | Na |
| 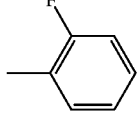 | 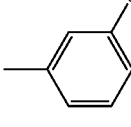 | Na |
| 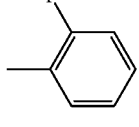 | 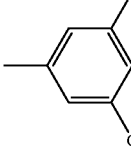 | Na |
| 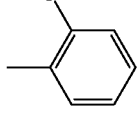 | | Na |

TABLE 2-continued
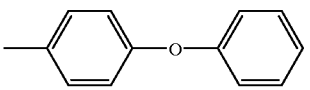
(Ic)
| R[4] | R[5] | M |
|---|---|---|
| 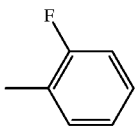 |  | Na |
| 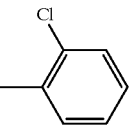 |  | Na |
| 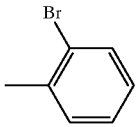 | 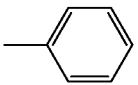 | Na |
| 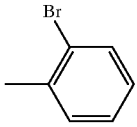 | 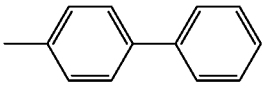 | Na |
| 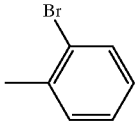 | 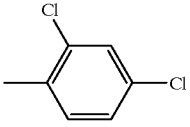 | Na |
| 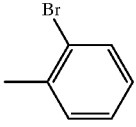 | 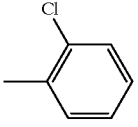 | Na |
| 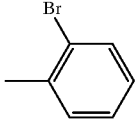 | 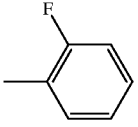 | Na |
| 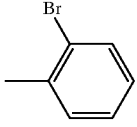 |  | Na |

TABLE 2-continued
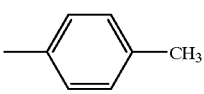
(Ic)
| R⁴ | R⁵ | M |
|---|---|---|
| 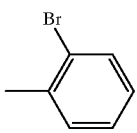 4-CH₃-C₆H₄- | 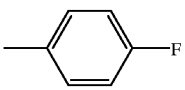 2-Br-C₆H₄- | Na |
| 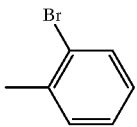 4-F-C₆H₄- | 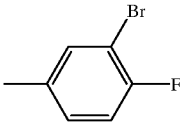 2-Br-C₆H₄- | Na |
| 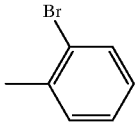 3-Br-4-F-C₆H₃- |  2-Br-C₆H₄- | Na |
| 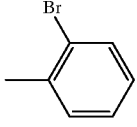 4-Br-C₆H₄- | 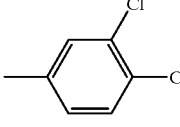 2-Br-C₆H₄- | Na |
| 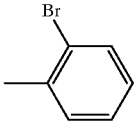 3,4-Cl₂-C₆H₃- | 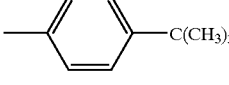 2-Br-C₆H₄- | Na |
| 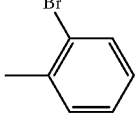 4-C(CH₃)₃-C₆H₄- | 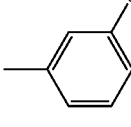 2-Br-C₆H₄- | Na |
| 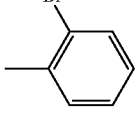 3-Cl-C₆H₄- | 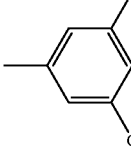 2-Br-C₆H₄- | Na |
| 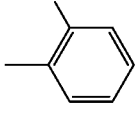 3,5-Cl₂-C₆H₃- | 2-Br-C₆H₄- | Na |

TABLE 2-continued (Ic)

[Structure: R⁴-C(-O-CH-R⁵)(-CH₂-N(triazole)-S⁻M⁺), with an epoxide between C and CH, and the N connected to a 1,2,4-triazole ring bearing S⁻M⁺]

| R⁴ | R⁵ | M |
|---|---|---|
| 4-phenoxyphenyl | 2-bromophenyl | Na |
| —CH₃ | 2-chlorophenyl | Na |
| —CH₃ | 2-fluorophenyl | Na |
| —CH₃ | 2-bromophenyl | Na |
| —C(CH₃)₃ | 2-chlorophenyl | Na |
| 1-chlorocyclopropyl | 2-chlorophenyl | Na |
| phenyl | 2-chlorophenyl | HN(C₂H₅)₃ |
| 4-chlorophenyl | 2-chlorophenyl | HN(C₂H₅)₃ |

TABLE 2-continued $$\text{(Ic)}$$

[Structure: oxirane ring with $R^4$ and $R^5$ substituents, connected via CH$_2$ to N of 1,2,4-triazole bearing S$^⊖$M$^⊕$ at position 5]

| R$^4$ | R$^5$ | M |
|---|---|---|
| 4-biphenyl | 2-chlorophenyl | HN(C$_2$H$_5$)$_3$ |
| 2,4-dichlorophenyl | 2-chlorophenyl | HN(C$_2$H$_5$)$_3$ |
| 2-chlorophenyl | 2-chlorophenyl | HN(C$_2$H$_5$)$_3$ |
| 2-fluorophenyl | 2-chlorophenyl | HN(C$_2$H$_5$)$_3$ |
| 4-methylphenyl | 2-chlorophenyl | HN(C$_2$H$_5$)$_3$ |
| 3-bromo-4-fluorophenyl | 2-chlorophenyl | HN(C$_2$H$_5$)$_3$ |
| 4-bromophenyl | 2-chlorophenyl | HN(C$_2$H$_5$)$_3$ |
| 3,4-dichlorophenyl | 2-chlorophenyl | HN(C$_2$H$_5$)$_3$ |

TABLE 2-continued
(Ic)
| R⁴ | R⁵ | M |
|---|---|---|
| 4-F-C₆H₄— | 2-Cl-C₆H₄— | HN(C₂H₅)₃ |
| 4-C(CH₃)₃-C₆H₄— | 2-Cl-C₆H₄— | HN(C₂H₅)₃ |
| 3-Cl-C₆H₄— | 2-Cl-C₆H₄— | HN(C₂H₅)₃ |
| 3,5-Cl₂-C₆H₃— | 2-Cl-C₆H₄— | HN(C₂H₅)₃ |
| 4-PhO-C₆H₄— | 2-Cl-C₆H₄— | HN(C₂H₅)₃ |
| 4-OCF₃-C₆H₄— | 2-Cl-C₆H₄— | HN(C₂H₅)₃ |
| 4-SCF₃-C₆H₄— | 2-Cl-C₆H₄— | HN(C₂H₅)₃ |
| 4-F-C₆H₄— | 2-OCHF₂-C₆H₄— | HN(C₂H₅)₃ |

TABLE 2-continued
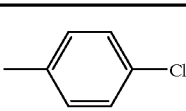
(Ic)
| R⁴ | R⁵ | M |
|---|---|---|
| 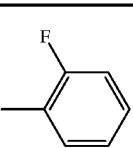 | 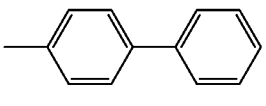 | HN(C₂H₅)₃ |
| 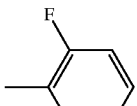 | 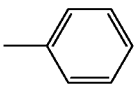 | HN(C₂H₅)₃ |
| 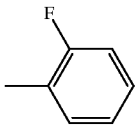 | 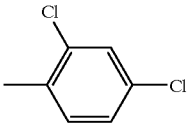 | HN(C₂H₅)₃ |
| 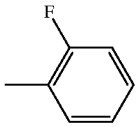 | 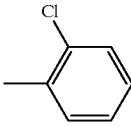 | HN(C₂H₅)₃ |
| 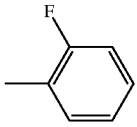 | 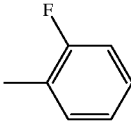 | HN(C₂H₅)₃ |
| 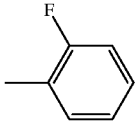 | 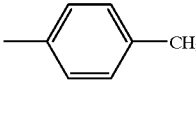 | HN(C₂H₅)₃ |
| 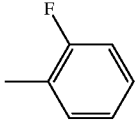 | 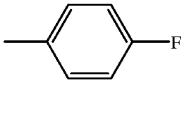 | HN(C₂H₅)₃ |
| 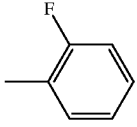 | | HN(C₂H₅)₃ |

TABLE 2-continued
(Ic)
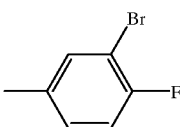
| R⁴ | R⁵ | M |
|---|---|---|
| 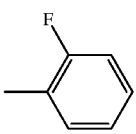 | 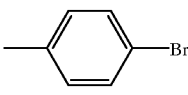 | HN(C₂H₅)₃ |
| 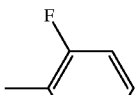 | 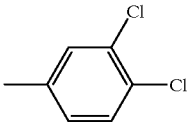 | HN(C₂H₅)₃ |
| 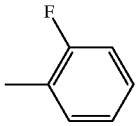 | 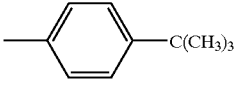 | HN(C₂H₅)₃ |
| 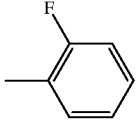 | 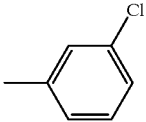 | HN(C₂H₅)₃ |
| 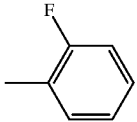 | 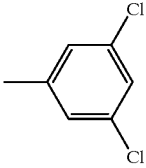 | HN(C₂H₅)₃ |
| 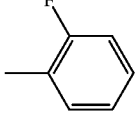 | 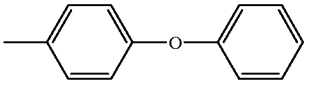 | HN(C₂H₅)₃ |
| 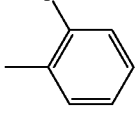 | 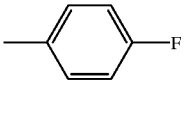 | HN(C₂H₅)₃ |
| 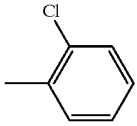 | | HN(C₂H₅)₃ |

TABLE 2-continued (Ic)

$$R^4-\underset{\underset{\underset{N\diagdown}{\overset{|}{CH_2}}}{\overset{O}{|}}}{C}-CH-R^5$$

(triazole-S⁻ M⁺ attached via CH₂)

| R⁴ | R⁵ | M |
|---|---|---|
| 4-Cl-C₆H₄– | 2-Br-C₆H₄– | ½ Cu |
| C₆H₅– | 2-Br-C₆H₄– | ½ Cu |
| 4-biphenyl– | 2-Br-C₆H₄– | ½ Cu |
| 2,4-diCl-C₆H₃– | 2-Br-C₆H₄– | ½ Cu |
| 2-Cl-C₆H₄– | 2-Br-C₆H₄– | ½ Cu |
| 2-F-C₆H₄– | 2-Br-C₆H₄– | ½ Cu |
| 4-CH₃-C₆H₄– | 2-Br-C₆H₄– | ½ Cu |
| 4-F-C₆H₄– | 2-Br-C₆H₄– | ½ Cu |

TABLE 2-continued
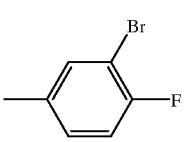
(Ic)
| R⁴ | R⁵ | M |
|---|---|---|
| 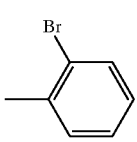 | 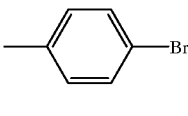 | ½ Cu |
| 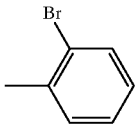 | 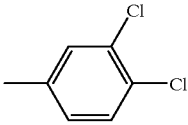 | ½ Cu |
| 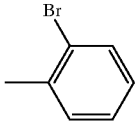 | 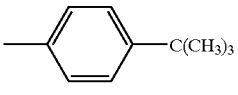 | ½ Cu |
| 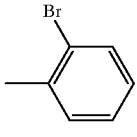 | 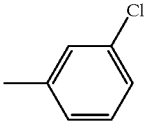 | ½ Cu |
| 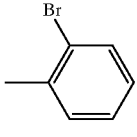 | 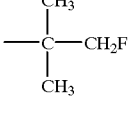 | ½ Cu |
| 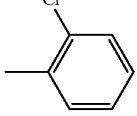 | 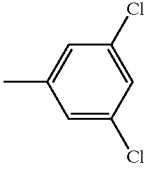 | ½ Cu |
| 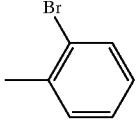 | 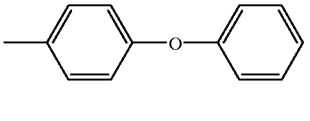 | ½ Cu |
| 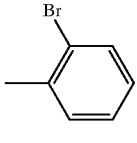 | | ½ Cu |

TABLE 2-continued
| R6 | R7 | M | X1m |
|---|---|---|---|
| —CH$_3$ | —CH$_3$ | Na | 4-Br |
| —CH$_3$ | —CH$_3$ | Na | 4-F |
| —CH$_3$ | —CH$_3$ | Na | 2,4-Cl$_2$ |
| —CH$_3$ | H | Na | 4-Cl |
| —CH$_3$ | —CH$_3$ | Na | — |
| —CH$_3$ | —CH$_3$ | Na | 4-CH$_3$ |
| —CH$_3$ | —CH$_3$ | Na | 2-F, 4-Cl |
| —C$_2$H$_5$ | H | Na | 4-Cl |
| —C$_2$H$_5$ | —C$_2$H$_5$ | Na | 4-Cl |
| —C$_3$H$_7$-n | H | Na | 4-Cl |
| —C$_2$H$_5$ | H | Na | 2,4-Cl$_2$ |
| —C$_2$H$_5$ | H | Na | 4-F |
| —C$_2$H$_5$ | H | Na | 4-Br |

TABLE 3-continued

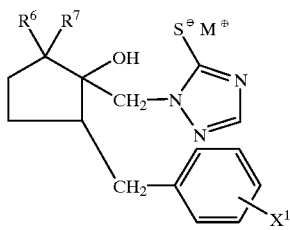

(Id)

| R6 | R7 | M | X1m |
|---|---|---|---|
| —C₂H₅ | H | Na | 2-F |
| —C₂H₅ | H | Na | 4-C₄H₉-t |
| —C₃H₇-i | H | Na | 4-Cl |
| —C₅H₁₁-n | H | Na | 4-Cl |
| —CH₃ | —CH₃ | Na | 4-(phenyl) |
| —CH₃ | —CH₃ | Na | 4-C₄H₉-t |
| —C₄H₉-n | H | Na | 4-Cl |
| —C₄H₉-i | H | Na | 4-Cl |
| —CH₃ | —C₂H₅ | Na | 4-Cl |
| —CH₃ | —CH₃ | HN(C₂H₅)₃ | 4-Cl |
| —CH₃ | —CH₃ | ½ Cu | 4-Br |
| —CH₃ | —CH₃ | ½ Cu | 4-F |
| —CH₃ | —CH₃ | ½ Cu | 2,4-Cl₂ |
| —CH₃ | H | ½ Cu | 4-Cl |
| —CH₃ | —CH₃ | ½ Cu | — |
| —CH₃ | —CH₃ | ½ Cu | 4-CH₃ |
| —CH₃ | —CH₃ | ½ Cu | 2-F, 4-Cl |
| —C₂H₅ | H | ½ Cu | 4-Cl |
| —C₂H₅ | —C₂H₅ | ½ Cu | 4-Cl |
| —C₃H₇-n | H | ½ Cu | 4-Cl |
| —C₂H₅ | H | ½ Cu | 2,4-Cl₂ |
| —C₂H₅ | H | ½ Cu | 4-F |
| —C₂H₅ | H | ½ Cu | 4-Br |
| —C₂H₅ | H | ½ Cu | 4-(phenyl) |
| —C₂H₅ | H | ½ Cu | 4-C₄H₉-t |
| —C₃H₇-I | H | ½ Cu | 4-Cl |
| —C₅H₁₁-n | H | ½ Cu | 4-Cl |
| —CH₃ | —CH₃ | ½ Cu | 4-(phenyl) |
| —CH₃ | —CH₃ | ½ Cu | 4-C₄H₉-t |
| —C₄H₉-n | H | ½ Cu | 4-Cl |
| —C₄H₉-i | H | ½ Cu | 4-Cl |
| —CH₃ | —C₂H₅ | ½ Cu | 4-Cl |
| —CH₃ | —CH₃ | ½ Cu | 2-Cl |
| —CH₃ | —CH₃ | ½ Cu | 2,3-Cl₂ |
| —CH₃ | —CH₃ | ½ Cu | 4-CF₃ |
| —CH₃ | —CH₃ | ½ Cu | 4-OCF₃ |
| —CH₃ | —CH₃ | ½ Cu | 4-Cl |

TABLE 4

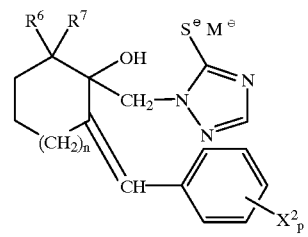

(Ie)

| R⁸ | R⁹ | M | X²p | n |
|---|---|---|---|---|
| —CH₃ | —CH₃ | Na | 4-Br | 0 |
| —CH₃ | —CH₃ | Na | 4-F | 0 |
| —CH₃ | —CH₃ | Na | 2,4-Cl₂ | 0 |
| —CH | H | Na | 4-Cl | 0 |
| —CH₃ | —CH₃ | Na | — | 0 |
| —CH₃ | —CH₃ | Na | 4-CH₃ | 0 |
| —CH₃ | —CH₃ | Na | 2-F, 4-Cl | 0 |
| —C₂H₅ | H | Na | 4-Cl | 0 |
| —C₂H₅ | —C₂H₅ | Na | 4-Cl | 0 |
| —C₃H₇-n | H | Na | 4-Cl | 0 |
| —C₂H₅ | H | Na | 2,4-Cl₂ | 0 |
| —C₂H₅ | H | Na | 4-F | 0 |
| —C₂H₅ | H | Na | 4-Br | 0 |
| —C₂H₅ | H | Na | 4-NO₂ | 0 |
| —C₂H₅ | H | Na | 4-C₄H₉-t | 0 |
| —C₃H₇-i | H | Na | 4-Cl | 0 |
| —C₅H₁₁-n | H | Na | 4-Cl | 0 |
| —CH₃ | —CH₃ | Na | 4-CN | 0 |
| —CH₃ | —CH₃ | Na | 4-C₄H₉-t | 0 |
| —C₄H₉-n | H | Na | 4-Cl | 0 |
| —C₄H₉-i | H | Na | 4-Cl | 0 |
| —CH₃ | —C₂H₅ | Na | 4-Cl | 0 |
| —CH₃ | —CH₃ | Na | 4-Cl | 0 |
| —CH₃ | —CH₃ | ½ Cu | 4-Br | 0 |
| —CH₃ | —CH₃ | ½ Cu | 4-F | 0 |
| —CH₃ | —CH₃ | ½ Cu | 2,4-Cl₂ | 0 |
| —CH₃ | H | ½ Cu | 4-Cl | 0 |
| —CH₃ | —CH₃ | ½ Cu | — | 0 |
| —CH₃ | —CH₃ | ½ Cu | 4-CH₃ | 0 |
| —CH₃ | —CH₃ | ½ Cu | 2-F, 4-Cl | 0 |
| —C₂H₅ | H | ½ Cu | 4-Cl | 0 |
| —C₂H₅ | —C₂H₅ | ½ Cu | 4-Cl | 0 |
| —C₃H₇-n | H | ½ Cu | 4-Cl | 0 |
| —C₂H₅ | H | ½ Cu | 2,4-Cl₂ | 0 |
| —C₂H₅ | H | ½ Cu | 4-F | 0 |
| —C₂H₅ | H | ½ Cu | 4-Br | 0 |
| —C₂H₅ | H | ½ Cu | 4-NO₂ | 0 |
| —C₂H₅ | H | ½ Cu | 4-C₄H₉-t | 0 |
| —C₃H₇-i | H | ½ Cu | 4-Cl | 0 |
| —C₅H₁₁-n | H | ½ Cu ½ Cu | 4-Cl | 0 |
| —CH₃ | —CH₃ | ½ Cu | 4-CN | 0 |
| —CH₃ | —CH₃ | ½ Cu | 4-C₄H₉-t | 0 |
| —C₄H₉-n | H | ½ Cu | 4-Cl | 0 |
| —C₄H₉-i | H | ½ Cu | 4-Cl | 0 |
| —CH₃ | —C₂H₅ | ½ Cu | 4-Cl | 0 |
| —CH₃ | —CH₃ | Na | 4-OCH₃ | 0 |
| —CH₃ | —CH₃ | Na | 2-OCH₃ | 0 |
| —CH₃ | —CH₃ | Na | 2-CF₃ | 0 |
| —CH₃ | —CH₃ | Na | 4-CF₃ | 0 |
| —CH₃ | —CH₃ | Na | 2-OCF₃ | 0 |
| —CH₃ | —CH₃ | Na | 2-OCHF₂ | 0 |
| —CH₃ | —CH₃ | Na | 4-OCF₃ | 0 |
| —CH₃ | —CH₃ | ½ Cu | 4-OCH₃ | 0 |
| —CH₃ | —CH₃ | ½ Cu | 2-OCH₃ | 0 |
| —CH₃ | —CH₃ | ½ Cu | 2-CF₃ | 0 |
| —CH₃ | —CH₃ | ½ Cu | 4-CF₃ | 0 |
| —CH₃ | —CH₃ | ½ Cu | 2-OCF₃ | 0 |
| —CH₃ | —CH₃ | ½ Cu | 2-OCHF₂ | 0 |
| —CH₃ | —CH₃ | ½ Cu | 4-OCF₃ | 0 |
| —CH₃ | —CH₃ | Na | 4-Br | 1 |
| —CH₃ | —CH₃ | Na | 4-F | 1 |
| —CH₃ | —CH₃ | Na | 2,4-Cl₂ | 1 |
| —CH₃ | H | Na | 4-Cl | 1 |

TABLE 4-continued

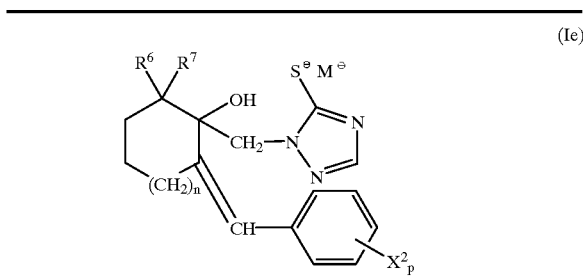

(Ie)

| R[8] | R[9] | M | X[2]p | n |
|---|---|---|---|---|
| —CH$_3$ | —CH$_3$ | Na | — | 1 |
| —CH$_3$ | —CH$_3$ | Na | 4-CH$_3$ | 1 |
| —CH$_3$ | —CH$_3$ | Na | 2-F, 4-Cl | 1 |
| —C$_2$H$_5$ | H | Na | 4-Cl | 1 |
| —C$_2$H$_5$ | —C$_2$H$_5$ | Na | 4-Cl | 1 |
| —C$_3$H$_7$-n | H | Na | 4-Cl | 1 |
| —C$_2$H$_5$ | H | Na | 2,4-Cl$_2$ | 1 |
| —C$_2$H$_5$ | H | Na | 4-F | 1 |
| —C$_2$H$_5$ | H | Na | 4-Br | 1 |
| —C$_2$H$_5$ | H | Na | 4-NO$_2$ | 1 |
| —C$_2$H$_5$ | H | Na | 4-C$_4$H$_9$-t | 1 |
| —C$_3$H$_7$-i | H | Na | 4-Cl | 1 |
| —C$_5$H$_{11}$-n | H | Na | 4-Cl | 1 |
| —CH$_3$ | —CH$_3$ | Na | 4-CN | 1 |
| —CH$_3$ | —CH$_3$ | Na | 4-C$_4$H$_9$-t | 1 |
| —C$_4$H$_9$-n | H | Na | 4-Cl | 1 |
| —CH$_3$ | —CH$_3$ | Na | 4-Cl | 1 |
| —CH$_3$ | —CH$_3$ | ½ Cu | 4-Cl | 1 |
| —C$_4$H$_9$-i | H | Na | 4-Cl | 1 |
| —CH$_3$ | —C$_2$H$_5$ | Na | 4-Cl | 1 |
| —CH$_3$ | —CH$_3$ | ½ Cu | 4-Cl | 1 |
| —CH$_3$ | —CH$_3$ | ½ Cu | 4-Br | 1 |
| —CH$_3$ | —CH$_3$ | ½ Cu | 4-F | 1 |
| —CH$_3$ | —CH$_3$ | ½ Cu | 2,4-Cl$_2$ | 1 |
| —CH$_3$ | H | ½ Cu | 4-Cl | 1 |
| —CH$_3$ | —CH$_3$ | ½ Cu | — | 1 |
| —CH$_3$ | —CH$_3$ | ½ Cu | 4-CH$_3$ | 1 |
| —CH$_3$ | —CH$_3$ | ½ Cu | 2-F, 4-Cl | 1 |
| —C$_2$H$_5$ | H | ½ Cu | 4-Cl | 1 |
| —C$_2$H$_5$ | —C$_2$H$_5$ | ½ Cu | 4-Cl | 1 |
| —C$_3$H$_7$-n | H | ½ Cu | 4-Cl | 1 |
| —C$_2$H$_5$ | H | ½ Cu | 2,4-Cl$_2$ | 1 |
| —C$_2$H$_5$ | H | ½ Cu | 4-F | 1 |
| —C$_2$H$_5$ | H | ½ Cu | 4-Br | 1 |
| —C$_2$H$_5$ | H | ½ Cu | 4-NO$_2$ | 1 |
| —C$_2$H$_5$ | H | ½ Cu | 4-C$_4$H$_9$-t | 1 |
| —C$_3$H$_7$-i | H | ½ Cu | 4-Cl | 1 |
| —C$_5$H$_{11}$-n | H | ½ Cu | 4-Cl | 1 |
| —CH$_3$ | —CH$_3$ | ½ Cu | 4-CN | 1 |
| —CH$_3$ | —CH$_3$ | ½ Cu | 4-C$_4$H$_9$-t | 1 |
| —C$_4$H$_9$-n | H | ½ Cu | 4-Cl | 1 |
| —C$_4$H$_9$-i | H | ½ Cu | 4-Cl | 1 |
| —CH$_3$ | —C$_2$H$_5$ | ½ Cu | 4-Cl | 1 |
| —CH$_3$ | —CH$_3$ | Na | 4-OCH$_3$ | 1 |
| —CH$_3$ | —CH$_3$ | Na | 2-OCH$_3$ | 1 |
| —CH$_3$ | —CH$_3$ | Na | 2-CF$_3$ | 1 |
| —CH$_3$ | —CH$_3$ | Na | 4-CF$_3$ | 1 |
| —CH$_3$ | —CH$_3$ | Na | 2-OCF$_3$ | 1 |
| —CH$_3$ | —CH$_3$ | Na | 2-OCHF$_2$ | 1 |
| —CH$_3$ | —CH$_3$ | Na | 4-OCF$_3$ | 1 |
| —CH$_3$ | —CH$_3$ | ½ Cu | 4-OCH$_3$ | 1 |
| —CH$_3$ | —CH$_3$ | ½ Cu | 2-OCH$_3$ | 1 |
| —CH$_3$ | —CH$_3$ | ½ Cu | 2-CF$_3$ | 1 |
| —CH$_3$ | —CH$_3$ | ½ Cu | 4-CF$_3$ | 1 |
| —CH$_3$ | —CH$_3$ | ½ Cu | 2-OCF$_3$ | 1 |
| —CH$_3$ | —CH$_3$ | ½ Cu | 2-OCHF$_2$ | 1 |
| —CH$_3$ | —CH$_3$ | ½ Cu | 4-OCF$_3$ | 1 |
| —CH$_3$ | —CH$_3$ | Na | 2-Cl | 0 |
| —CH$_3$ | —CH$_3$ | Na | 2,3-Cl$_2$ | 0 |
| —CH$_3$ | —CH$_3$ | Na | 2-Cl | 1 |
| —CH$_3$ | —CH$_3$ | HN(C$_2$H$_5$)$_3$ | 4-Cl | 0 |

TABLE 5

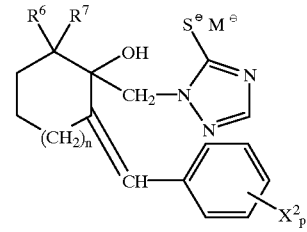

(If)

| R[10] | R[11] | R[12] | M |
|---|---|---|---|
| phenyl | —CH$_3$ | —CH$_3$ | Na |
| 4-methylphenyl | —CH$_3$ | —CH$_3$ | Na |

TABLE 5-continued
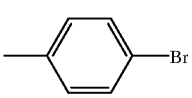
(If)
| R¹⁰ | R¹¹ | R¹² | M |
|---|---|---|---|
| 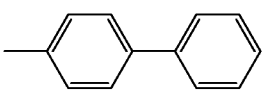 | —CH₃ | —CH₃ | Na |
| 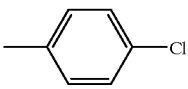 | —CH₃ | —CH₃ | Na |
| 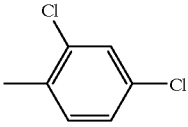 | —CH₃ | —CH₃ | Na |
| 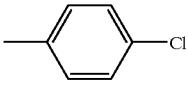 | —CH₃ | —CH₃ | Na |
| 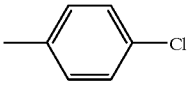 | —C₄H₉-n | —CH₃ | Na |
| 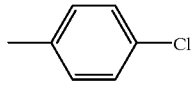 |  | —CH₃ | Na |
|  | 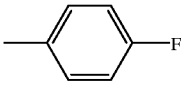 | —CH₃ | Na |
| 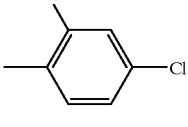 | —CH₃ | —CH₃ | Na |
| 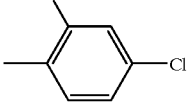 | —C₄H₉-n | —CH₃ | Na |
| 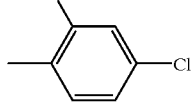 |  | —CH₃ | Na |

TABLE 5-continued (If)

$$\begin{array}{c} R^{12} \\ | \\ R^{10}-Si-R^{11} \\ | \\ CH_2 \\ | \\ N-N \\ \diagdown / \\ N \end{array} S^{\ominus} M^{\oplus}$$

| R$^{10}$ | R$^{11}$ | R$^{12}$ | M |
|---|---|---|---|
| 2,4-dichlorophenyl | phenyl | —CH$_3$ | Na |
| 4-chlorophenyl | phenyl | —CH$_3$ | Na |
| 4-fluorophenyl | phenyl | —CH$_3$ | Na |
| phenyl | —C$_4$H$_9$-n | —CH$_3$ | Na |
| 4-fluorophenyl | —C$_4$H$_9$-n | —CH$_3$ | Na |
| 4-biphenyl | 4-biphenyl | —CH$_3$ | Na |
| 4-biphenyl | —C$_4$H$_9$-n | —CH$_3$ | Na |
| 4-biphenyl | phenyl | —CH$_3$ | Na |
| phenyl | —CH$_3$ | —CH$_3$ | HN(C$_2$H$_5$)$_3$ |
| 4-methylphenyl | —CH$_3$ | —CH$_3$ | HN(C$_2$H$_5$)$_3$ |
| 4-bromophenyl | —CH$_3$ | —CH$_3$ | HN(C$_2$H$_5$)$_3$ |

TABLE 5-continued $$\underset{\substack{R^{10}-\underset{|}{Si}-R^{11}\\CH_2}}{R^{12}}$$

(If)

[Structure: 1,2,4-triazole ring with N-CH2 linkage to Si, and S⁻ M⁺ substituent on the adjacent carbon]

| R¹⁰ | R¹¹ | R¹² | M |
|---|---|---|---|
| 4-biphenylyl | —CH₃ | —CH₃ | HN(C₂H₅)₃ |
| 4-chlorophenyl | —CH₃ | —CH₃ | HN(C₂H₅)₃ |
| 2,4-dichlorophenyl | —CH₃ | —CH₃ | HN(C₂H₅)₃ |
| 4-chlorophenyl | —C₄H₉-n | —CH₃ | HN(C₂H₅)₃ |
| 4-chlorophenyl | 4-chlorophenyl | —CH₃ | HN(C₂H₅)₃ |
| phenyl | phenyl | —CH₃ | HN(C₂H₅)₃ |
| 4-fluorophenyl | —CH₃ | —CH₃ | HN(C₂H₅)₃ |
| 2,4-dichlorophenyl | —C₄H₉-n | —CH₃ | HN(C₂H₅)₃ |
| 2,4-dichlorophenyl | 2,4-dichlorophenyl | —CH₃ | HN(C₂H₅)₃ |
| 2,4-dichlorophenyl | phenyl | —CH₃ | HN(C₂H₅)₃ |

TABLE 5-continued $$\underset{\underset{N-N}{\overset{R^{10}-\underset{CH_2}{\overset{R^{12}}{\underset{|}{Si}}}-R^{11}}{|}}}{\overset{(If)}{\underset{N}{\bigwedge}}} S^{\ominus} M^{\oplus}$$

| R$^{10}$ | R$^{11}$ | R$^{12}$ | M |
|---|---|---|---|
| 4-F-C$_6$H$_4$— | C$_6$H$_5$— | —CH$_3$ | HN(C$_2$H$_5$)$_3$ |
| 4-F-C$_6$H$_4$— | C$_6$H$_5$— | —CH$_3$ | HN(C$_2$H$_5$)$_3$ |
| C$_6$H$_5$— | —C$_4$H$_9$-n | —CH$_3$ | HN(C$_2$H$_5$)$_3$ |
| 4-F-C$_6$H$_4$— | —C$_4$H$_9$-n | —CH$_3$ | HN(C$_2$H$_5$)$_3$ |
| 4-biphenyl— | 4-biphenyl— | —CH$_3$ | HN(C$_2$H$_5$)$_3$ |
| 4-biphenyl— | —C$_4$H$_9$-n | —CH$_3$ | HN(C$_2$H$_5$)$_3$ |
| 4-biphenyl— | C$_6$H$_5$— | —CH$_3$ | HN(C$_2$H$_5$)$_3$ |
| 4-F-C$_6$H$_4$— | 4-F-C$_6$H$_4$— | —CH$_3$ | Na |
| 4-F-C$_6$H$_4$— | 4-F-C$_6$H$_4$— | —CH$_3$ | HN(C$_2$H$_5$)$_3$ |
| 4-F-C$_6$H$_4$— | 4-F-C$_6$H$_4$— | —CH$_3$ | ½ Cu |

TABLE 6

(Ig)

[Structure: 1,2,4-triazole-CH2-C(OH)(R13)-CH2-N(triazole)-S⁻M⁺ — a compound with OH, R13, two CH2 groups connecting two triazole rings, one bearing S⁻M⁺]

| R¹³ | M |
|---|---|
| 4-chlorophenyl | Na |
| phenyl | Na |
| 4-fluorophenyl | Na |
| 2,4-dichlorophenyl | Na |
| 4-methylphenyl | Na |
| 4-biphenyl | Na |
| 4-methoxyphenyl | Na |
| 4-phenoxyphenyl | Na |
| 2-(trifluoromethyl)phenyl | Na |
| —C₄H₉-n | Na |
| —C(CH₃)₃ | Na |
| —CH(CH₃)₂ | Na |
| —C(CH₂Cl)₂CH₃ (1,3-dichloro-2-methylpropan-2-yl) | Na |

TABLE 6-continued (Ig)

| R¹³ | M |
|---|---|
| —C(CH₂F)₂CH₃ (1,3-difluoro-2-methylpropan-2-yl) | Na |
| —CH₂—CH(CH₃)₂ | Na |
| cyclopropyl | Na |
| cyclopentyl | Na |
| cyclohexyl | Na |
| 1-methylcyclopropyl | Na |
| 1-chlorocyclopropyl | Na |
| 1-fluorocyclopropyl | Na |
| 1-methylcyclohexyl | Na |
| —CH₂—(4-chlorophenyl) | Na |
| 2-(difluoromethoxy)phenyl | Na |
| —CH₂—(2-chlorophenyl) | Na |

TABLE 6-continued (Ig)

[Structure: R13-C(OH)(CH2-triazole)(CH2-N(triazole)-S⁻M⁺)]

| R¹³ | M |
|---|---|
| —CH2—(2,3-dichlorophenyl) | Na |
| —CH2—C6H5 | Na |
| —CH2—(4-methoxyphenyl) | Na |
| —CH(CH3)—C2H5 | Na |
| —CH2—(4-fluorophenyl) | Na |
| —CH(CH3)—C6H5 | Na |
| —CH(CH3)—(4-chlorophenyl) | Na |
| —CH(CH3)—(4-fluorophenyl) | Na |
| —CH(CH3)—(4-trifluoromethylphenyl) | Na |
| —CH(CH3)—(4-methoxyphenyl) | Na |
| —CH(CH3)—(4-trifluoromethoxyphenyl) | Na |
| —(2,6-dichlorophenyl) | Na |
| —(4-trifluoromethoxyphenyl) | Na |
| —(2,6-dichloro-4-chlorophenyl) | Na |
| —(3,4-dichlorophenyl) | Na |
| —(4-chlorophenyl) | HN(C2H5)3 |
| —C6H5 | HN(C2H5)3 |
| —(4-fluorophenyl) | HN(C2H5)3 |
| —(2,4-dichlorophenyl) | HN(C2H5)3 |

TABLE 6-continued

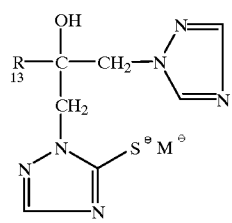

(Ig)

| R¹³ | M |
|---|---|
| 4-methylphenyl (–C₆H₄–CH₃) | HN(C₂H₅)₃ |
| 4-phenylphenyl (biphenyl) | HN(C₂H₅)₃ |
| 4-methoxyphenyl (–C₆H₄–OCH₃) | HN(C₂H₅)₃ |
| 4-phenoxyphenyl (–C₆H₄–O–C₆H₅) | HN(C₂H₅)₃ |
| 2-(trifluoromethyl)phenyl | HN(C₂H₅)₃ |
| —C₄H₉-n | ½ Cu |
| —C(CH₃)₃ | ½ Cu |
| —CH(CH₃)₂ | ½ Cu |
| —C(CH₂Cl)₂CH₃ | HN(C₂H₅)₃ |
| —C(CH₃)₂CH₂F | HN(C₂H₅)₃ |
| —CH₂—CH(CH₃)₂ | ½ Cu |
| cyclopropyl | ½ Cu |
| cyclopentyl | HN(C₂H₅)₃ |
| cyclohexyl | HN(C₂H₅)₃ |

TABLE 6-continued

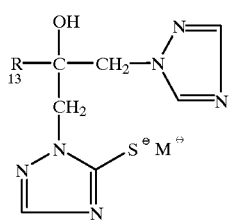

(Ig)

| R¹³ | M |
|---|---|
| 1-methylcyclopropyl | HN(C₂H₅)₃ |
| 1-chlorocyclopropyl | HN(C₂H₅)₃ |
| 1-fluorocyclopropyl | HN(C₂H₅)₃ |
| 1-methylcyclohexyl | HN(C₂H₅)₃ |
| —CH₂—(4-chlorophenyl) | HN(C₂H₅)₃ |
| 2-(difluoromethoxy)phenyl | HN(C₂H₅)₃ |
| —CH₂—(2-chlorophenyl) | HN(C₂H₅)₃ |
| —CH₂—(2,3-dichlorophenyl) | HN(C₂H₅)₃ |
| —CH₂—C₆H₅ | HN(C₂H₅)₃ |
| —CH₂—(4-methoxyphenyl) | HN(C₂H₅)₃ |
| —CH(CH₃)—C₂H₅ | HN(C₂H₅)₃ |

TABLE 6-continued (Ig)

[Structure: 1,2,4-triazole-thiolate with CH2-C(OH)(R13)-CH2-triazole linker]

| R13 | M |
|---|---|
| —CH2—C6H4—4-F | HN(C2H5)3 |
| —CH(CH3)—C6H5 | HN(C2H5)3 |
| —CH(CH3)—C6H4—4-Cl | HN(C2H5)3 |
| —CH(CH3)—C6H4—4-F | HN(C2H5)3 |
| —CH(CH3)—C6H4—4-CF3 | HN(C2H5)3 |
| —CH(CH3)—C6H4—4-OCH3 | HN(C2H5)3 |
| —CH(CH3)—C6H4—4-OCF3 | HN(C2H5)3 |
| 2,6-Cl2-C6H3— | HN(C2H5)3 |
| 4-OCF3-C6H4— | HN(C2H5)3 |

TABLE 6-continued (Ig)

| R13 | M |
|---|---|
| 2,4,6-Cl3-C6H2— | HN(C2H5)3 |
| 3,4-Cl2-C6H3— | HN(C2H5)3 |
| 2,4-F2-C6H3— | Na |
| 2,4-F2-C6H3— | HN(C2H5)3 |
| 2,4-F2-C6H3— | ½ Cu |

TABLE 7

(Ih)

[Structure: X4s-phenyl-Y2-C(CH3)2-CH(OH)-CH(R14)-triazole-thiolate M+]

| X4s | Y2 | R14 | M |
|---|---|---|---|
| 4-Cl | CH2 | H | Na |
| 4-CF3 | CH2 | H | Na |
| 4-OCF3 | CH2 | H | Na |
| 2,4-Cl2 | CH2 | H | Na |
| 4-CH3 | CH2 | H | Na |
| 2-Cl | CH2 | H | Na |
| 2-F | CH2 | H | Na |
| 4-F | CH2 | H | Na |
| 2-OCHF2 | CH2 | H | Na |

TABLE 7-continued

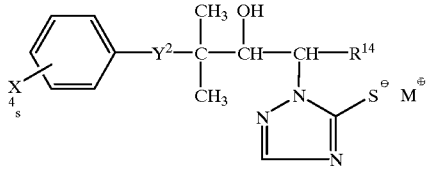

(Ih)

| $X^4{}_s$ | $Y^2$ | $R^{14}$ | M |
|---|---|---|---|
| 4-Cl | O | H | Na |
| 4-CF$_3$ | O | H | Na |
| 4-OCF$_3$ | O | H | Na |
| 2,4-Cl$_2$ | O | H | Na |
| 4-CH$_3$ | O | H | Na |
| 2-Cl | O | H | Na |
| 2-F | O | H | Na |
| 4-F | O | H | Na |
| 2-OCHF$_2$ | O | H | Na |
| 4-Cl | — | H | Na |
| 4-CF$_3$ | — | H | Na |
| 4-OCF$_3$ | — | H | Na |
| 2,4-Cl$_2$ | — | H | Na |
| 4-CH$_3$ | — | H | Na |
| 2-Cl | — | H | Na |
| 2-F | — | H | Na |
| 4-F | — | H | Na |
| 2-OCHF$_2$ | — | H | Na |
| 4-Cl | CH$_2$ | —CH$_3$ | Na |
| 4-CF$_3$ | CH$_2$ | —CH$_3$ | Na |
| 4-OCF$_3$ | CH$_2$ | —CH$_3$ | Na |
| 2,4-Cl$_2$ | CH$_2$ | —CH$_3$ | Na |
| 4-CH$_3$ | CH$_2$ | —CH$_3$ | Na |
| 2-Cl | CH$_2$ | —CH$_3$ | Na |
| 2-F | CH$_2$ | —CH$_3$ | Na |
| 4-F | CH$_2$ | —CH$_3$ | Na |
| 2-OCHF$_2$ | CH$_2$ | —CH$_3$ | Na |
| 4-Cl | O | —CH$_3$ | Na |
| 4-CF$_3$ | O | —CH$_3$ | Na |
| 2,4-Cl$_2$ | O | —CH$_3$ | Na |
| 4-OCF$_3$ | O | —CH$_3$ | Na |
| 2-F | O | —CH$_3$ | Na |
| 2-OCHF$_2$ | O | —CH$_3$ | Na |
| 4-Cl | — | —CH$_3$ | Na |
| 4-CF$_3$ | — | —CH$_3$ | Na |
| 2,4-Cl$_2$ | — | —CH$_3$ | Na |
| 4-OCF$_3$ | — | —CH$_3$ | Na |
| 2-F | — | —CH$_3$ | Na |
| 2-OCHF$_2$ | — | —CH$_3$ | Na |
| 4-Cl | CH$_2$ | C$_4$H$_9$-n | Na |
| 2,4-Cl$_2$ | CH$_2$ | —CH(CH$_3$)$_2$ | Na |
| 4-OCF$_3$ | CH$_2$ | —C(CH$_3$)$_3$ | Na |
| 4-Cl | CH$_2$ | cyclopropyl | Na |
| 4-Cl | CH$_2$ | chlorocyclopropyl | Na |
| 4-Cl | CH$_2$ | cyclopentyl | Na |
| 4-Cl | CH$_2$ | cyclohexyl | Na |
| 2,4,6-Cl$_3$ | CH$_2$ | —CH$_3$ | Na |

TABLE 7-continued

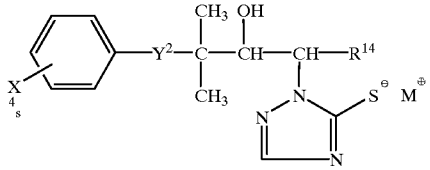

(Ih)

| $X^4{}_s$ | $Y^2$ | $R^{14}$ | M |
|---|---|---|---|
| 4-phenyl | CH$_2$ | —CH$_3$ | Na |
| 4-O-phenyl | CH$_2$ | —CH$_3$ | Na |
| 4-Cl | CH$_2$ | H | ½ Cu |
| 4-CF$_3$ | CH$_2$ | H | ½ Cu |
| 4-OCF$_3$ | CH$_2$ | H | ½ Cu |
| 2,4-Cl$_2$ | CH$_2$ | H | ½ Cu |
| 4-CH$_3$ | CH$_2$ | H | ½ Cu |
| 2-Cl | CH$_2$ | H | ½ Cu |
| 2-F | CH$_2$ | H | ½ Cu |
| 4-F | CH$_2$ | H | ½ Cu |
| 2-OCHF$_2$ | CH$_2$ | H | ½ Cu |
| 4-Cl | O | H | ½ Cu |
| 4-CF$_3$ | O | H | ½ Cu |
| 4-OCF$_3$ | O | H | ½ Cu |
| 2,4-Cl$_2$ | O | H | ½ Cu |
| 4-CH$_3$ | O | H | ½ Cu |
| 2-Cl | O | H | ½ Cu |
| 2-F | O | H | ½ Cu |
| 4-F | O | H | ½ Cu |
| 2-OCHF$_2$ | O | H | ½ Cu |
| 4-Cl | — | H | ½ Cu |
| 4-CF$_3$ | — | H | ½ Cu |
| 4-OCF$_3$ | — | H | ½ Cu |
| 2,4-Cl$_2$ | — | H | ½ Cu |
| 4-CH$_3$ | — | H | ½ Cu |
| 2-Cl | — | H | ½ Cu |
| 2-F | — | H | ½ Cu |
| 4-F | — | H | ½ Cu |
| 2-OCHF$_2$ | — | H | ½ Cu |
| 4-Cl | CH$_2$ | —CH$_3$ | ½ Cu |
| 4-CF$_3$ | CH$_2$ | —CH$_3$ | ½ Cu |
| 4-OCF$_3$ | CH$_2$ | —CH$_3$ | ½ Cu |
| 2,4-Cl$_2$ | CH$_2$ | —CH$_3$ | ½ Cu |
| 4-CH$_3$ | CH$_2$ | —CH$_3$ | ½ Cu |
| 2-Cl | CH$_2$ | —CH$_3$ | ½ Cu |
| 2-F | CH$_2$ | —CH$_3$ | ½ Cu |
| 4-F | CH$_2$ | —CH$_3$ | ½ Cu |
| 2-OCHF$_2$ | CH$_2$ | —CH$_3$ | ½ Cu |
| 4-Cl | O | —CH$_3$ | ½ Cu |
| 4-CF$_3$ | O | —CH$_3$ | ½ Cu |
| 2,4-Cl$_2$ | O | —CH$_3$ | ½ Cu |
| 4-OCF$_3$ | O | —CH$_3$ | ½ Cu |
| 2-F | O | —CH$_3$ | ½ Cu |
| 2-OCHF$_2$ | O | —CH$_3$ | ½ Cu |
| 4-Cl | — | —CH$_3$ | ½ Cu |
| 4-CF$_3$ | — | —CH$_3$ | ½ Cu |
| 2,4-Cl$_2$ | — | —CH$_3$ | ½ Cu |
| 4-OCF$_3$ | — | —CH$_3$ | ½ Cu |
| 2-F | — | —CH$_3$ | ½ Cu |
| 2-OCHF$_2$ | — | —CH$_3$ | ½ Cu |
| 4-Cl | CH$_2$ | —C$_4$H$_9$-n | ½ Cu |
| 2,4-Cl$_2$ | CH$_2$ | —CH(CH$_3$)$_2$ | ½ Cu |
| 4-OCF$_3$ | CH$_2$ | —C(CH$_3$)$_3$ | ½ Cu |
| 4-Cl | CH$_2$ | cyclopropyl | ½ Cu |

TABLE 7-continued (Ih)

[Structure: X⁴ₛ-phenyl-Y²-C(CH₃)₂-CH(OH)-CH(R¹⁴)-N(triazole-S⁻M⁺)]

| X⁴ₛ | Y² | R¹⁴ | M |
|---|---|---|---|
| 4-Cl | CH₂ | (chloromethylcyclopropyl) | HN(C₂H₅)₃ |
| 4-Cl | CH₂ | (methylcyclopentyl) | HN(C₂H₅)₃ |
| 4-Cl | CH₂ | (methylcyclohexyl) | HN(C₂H₅)₃ |
| 2,4,6-Cl₃ | CH₂ | —CH₃ | HN(C₂H₅)₃ |
| 4-(phenyl)phenyl | CH₂ | —CH₃ | HN(C₂H₅)₃ |
| 4-(phenoxy)phenyl-O- | —CH₂ | —CH₃ | HN(C₂H₅)₃ |
| 4-OCF₃ | CH₂ | —CH₃ | HN(C₂H₅)₃ |

TABLE 8

(Ii)

[Structure: X⁵ₜ-phenyl-Y³-CH-CH(OH)-R¹⁵ with triazole-S⁻M⁺]

| X⁵ₜ | R¹⁵ | M | Y³ |
|---|---|---|---|
| 2,4-Cl₂ | (methylphenyl) | Na | O |
| 4-Cl | (methylphenyl) | Na | O |
| 4-Br | —C(CH₃)₃ | Na | O |
| — | —C(CH₃)₃ | Na | O |
| 4-C(CH₃)₃ | —C(CH₃)₃ | Na | O |
| 2-Cl | —C(CH₃)₃ | Na | O |
| 3-Cl | —C(CH₃)₃ | Na | O |
| 4-F | —C(CH₃)₃ | Na | O |

TABLE 8-continued (Ii)

| X⁵ₜ | R¹⁵ | M | Y³ |
|---|---|---|---|
| 4-(methylphenyl) | —C(CH₃)₃ | Na | O |
| 2-(methylphenyl) | —C(CH₃)₃ | Na | O |
| 2,4-Cl₂ | —C(CH₃)₃ | Na | O |
| 2-CH₃, 4-Cl | —C(CH₃)₃ | Na | O |
| 3,4-(CH₃)₂ | —C(CH₃)₃ | Na | O |
| 2,4,5-Cl₃ | —C(CH₃)₃ | Na | O |
| 4-Cl | —CH₃ | Na | O |
| 4-Cl | —CH₂-phenyl | Na | O |
| 4-CF₃ | —C(CH₃)₃ | Na | O |
| 4-OCF₃ | —C(CH₃)₃ | Na | O |
| 2-OCHF₂ | —C(CH₃)₃ | Na | O |
| 4-OCH₃ | —C(CH₃)₃ | Na | O |
| 2,4-Cl₂ | (methylphenyl) | HN(C₂H₅)₃ | O |
| 4-Cl | (methylphenyl) | HN(C₂H₅)₃ | O |
| 4-Br | —C(CH₃)₃ | ½ Cu | O |
| — | —C(CH₃)₃ | ½ Cu | O |
| 4-C(CH₃)₃ | —C(CH₃)₃ | ½ Cu | O |
| 2-Cl | —C(CH₃)₃ | ½ Cu | O |
| 3-Cl | —C(CH₃)₃ | ½ Cu | O |
| 4-F | —C(CH₃)₃ | ½ Cu | O |
| 4-(methylphenyl) | —C(CH₃)₃ | HN(C₂H₅)₃ | O |
| 2-(methylphenyl) | —C(CH₃)₃ | HN(C₂H₅)₃ | O |
| 2,4-Cl₂ | —C(CH₃)₃ | ½ Cu | O |
| 2-CH₃, 4-Cl | —C(CH₃)₃ | ½ Cu | O |
| 3,4-(CH₃)₂ | —C(CH₃)₃ | ½ Cu | O |
| 2,4,5-Cl₃ | —C(CH₃)₃ | ½ Cu | O |
| 4-Cl | —CH₃ | ½ Cu | O |

TABLE 8-continued (Ii)

Structure: X⁵ₜ-phenyl-Y³-CH(-triazole-S⁻M⁺)-CH(OH)-R¹⁵

| X⁵ₜ | R¹⁵ | M | Y³ |
|---|---|---|---|
| 4-Cl | —CH₂—C₆H₅ | HN(C₂H₅)₃ | O |
| 4-CF₃ | —C(CH₃)₃ | ½ Cu | O |
| 4-OCF₃ | —C(CH₃)₃ | ½ Cu | O |
| 2-OCHF₂ | —C(CH₃)₃ | ½ Cu | O |
| 4-OCH₃ | —C(CH₃)₃ | ½ Cu | O |
| 4-Cl | —C(CH₃)₂CH₂F | Na | O |
| 4-Cl | —C(CH₂F)₂CH₃ | Na | O |
| 4-Cl | —C(CH₃)₂CH₂F | HN(C₂H₅)₃ | O |
| 4-Cl | —C(CH₂F)₂CH₃ | HN(C₂H₅)₃ | O |
| 2,4-Cl₂ | 4-CH₃—C₆H₄— | Na | CH₂ |
| 4-Cl | 4-CH₃—C₆H₄— | Na | CH₂ |
| 4-Br | —C(CH₃)₃ | Na | CH₂ |
| — | —C(CH₃)₃ | Na | CH₂ |
| 4-C(CH₃)₃ | —C(CH₃)₃ | Na | CH₂ |
| 2-Cl | —C(CH₃)₃ | Na | CH₂ |
| 3-Cl | —C(CH₃)₃ | Na | CH₂ |
| 4-F | —C(CH₃)₃ | Na | CH₂ |
| 4-CH₃—C₆H₄— | —C(CH₃)₃ | Na | CH₂ |
| 2-CH₃—C₆H₄— | —C(CH₃)₃ | Na | CH₂ |
| 2,4-Cl₂ | —C(CH₃)₃ | Na | CH₂ |
| 2-CH₃, 4-Cl | —C(CH₃)₃ | Na | CH₂ |
| 3,4-(CH₃)₂ | —C(CH₃)₃ | Na | CH₂ |
| 2,4,5-Cl₃ | —C(CH₃)₃ | Na | CH₂ |
| 4-Cl | —CH₃ | Na | CH₂ |
| 4-Cl | —CH₂—C₆H₅ | Na | CH₂ |
| 4-CF₃ | —C(CH₃)₃ | Na | CH₂ |
| 4-OCF₃ | —C(CH₃)₃ | Na | CH₂ |
| 2-OCHF₂ | —C(CH₃)₃ | Na | CH₂ |
| 4-OCH₃ | —C(CH₃)₃ | Na | CH₂ |
| 2,4-Cl₂ | 4-CH₃—C₆H₄— | HN(C₂H₅)₃ | CH₂ |
| 4-Cl | 4-CH₃—C₆H₄— | HN(C₂H₅)₃ | CH₂ |
| 4-Br | —C(CH₃)₃ | ½ Cu | CH₂ |
| — | —C(CH₃)₃ | ½ Cu | CH₂ |
| 4-C(CH₃)₃ | —C(CH₃)₃ | ½ Cu | CH₂ |
| 2-Cl | —C(CH₃)₃ | ½ Cu | CH₂ |
| 3-Cl | —C(CH₃)₃ | ½ Cu | CH₂ |
| 4-F | —C(CH₃)₃ | ½ Cu | CH₂ |
| 4-CH₃—C₆H₄— | —C(CH₃)₃ | HN(C₂H₅)₃ | CH₂ |
| 2-CH₃—C₆H₄— | —C(CH₃)₃ | HN(C₂H₅)₃ | CH₂ |
| 2,4-Cl₂ | —C(CH₃)₃ | ½ Cu | CH₂ |
| 2-CH₃, 4-Cl | —C(CH₃)₃ | ½ Cu | CH₂ |
| 3,4-(CH₃)₂ | —C(CH₃)₃ | ½ Cu | CH₂ |
| 2,4,5-Cl₃ | —C(CH₃)₃ | ½ Cu | CH₂ |
| 4-Cl | —CH₃ | ½ Cu | CH₂ |
| 4-Cl | —CH₂—C₆H₅ | HN(C₂H₅)₃ | CH₂ |
| 4-CF₃ | —C(CH₃)₃ | ½ Cu | CH₂ |
| 4-OCF₃ | —C(CH₃)₃ | ½ Cu | CH₂ |
| 2-OCHF₂ | —C(CH₃)₃ | ½ Cu | CH₂ |
| 4-OCH₃ | —C(CH₃)₃ | ½ Cu | CH₂ |
| 4-Cl | —C(CH₃)₂CH₂F | Na | CH₂ |

TABLE 8-continued (Ii)
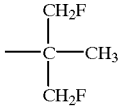

| $X^5_t$ | $R^{15}$ | M | $Y^3$ |
|---|---|---|---|
| 4-Cl | —C(CH₂F)(CH₃)(CH₂F) | Na | CH₂ |
| 4-Cl | —C(CH₃)(CH₂F)(CH₃) | HN(C₂H₅)₃ | CH₂ |
| 4-Cl | —C(CH₂F)(CH₃)(CH₂F) | HN(C₂H₅)₃ | CH₂ |
| 4-Cl | —C(CH₃)₃ | Na | O |
| 4-Cl | —C(CH₃)₃ | ½ Cu | O |
| 4-Cl | —C(CH₃)₃ | HN(C₂H₅)₃ | O |

TABLE 9

(Ik)
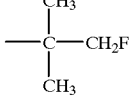

| $X^6_u$ | A | M |
|---|---|---|
| 2,4-Cl₂ | —(CH₂)₃— | Na |
| 2,4-Cl₂ | —(CH₂)₂— | Na |
| 4-Cl | —CH₂—CH(CH₃)— | Na |
| 4-CF₃ | —CH₂—CH(C₃H₇-n)— | Na |
| 2-Cl, 4-O-C₆H₄-Cl | —CH₂—CH₂— | Na |
| 2-Cl, 4-O-C₆H₄-Cl | —CH₂—CH(C₂H₅)— | Na |

TABLE 9-continued (Ik)
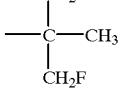

| $X^6_u$ | A | M |
|---|---|---|
| 4-F | —CH₂—CH(C₃H₇-n)— | Na |
| 4-OCF₃ | —CH₂—CH(C₃H₇-n)— | Na |
| 2,4-F₂ | —CH₂—CH(C₃H₇-n)— | Na |
| 2-OCHF₂ | —CH₂—CH(C₃H₇-n)— | Na |
| 2-Cl, 4-O-C₆H₄-Cl | —(CH₂)₃— | Na |
| 2,4,6-Cl₃ | —CH₂—CH(C₃H₇-n)— | Na |
| — | —CH₂—CH(C₃H₇-n)— | Na |
| 2,4-F₂ | —CH₂—CH(CH₃)— | Na |
| 2-Cl, 4-O-C₆H₄-Cl | —CH₂—CH(CH₃)— | Na |
| 2,4-Cl₂ | —CH(CH₃)—CH(CH₃)— | Na |
| 2-Cl, 4-O-C₆H₄-Cl | —CH(CH₃)—CH(CH₃)— | Na |
| 2,4-Cl₂ | —CH₂—CH(F)— | Na |
| 2-Cl, 4-O-C₆H₄-Cl | —CH₂—CH(C₄H₉-n)— | Na |

TABLE 9-continued (Ik)

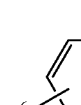

| $X^6_u$ | A | M |
|---|---|---|
| 2,4-Cl$_2$ | —CH$_2$—CH(C$_2$H$_5$)— | Na |
| 2,4-Cl$_2$ | —(CH$_2$)$_3$— | ½ Cu |
| 2,4-Cl$_2$ | —(CH$_2$)$_2$— | ½ Cu |
| 4-Cl | —CH$_2$—CH(CH$_3$)— | HN(C$_2$H$_5$)$_3$ |
| 4-CF$_3$ | —CH$_2$—CH(C$_3$H$_7$-n)— | HN(C$_2$H$_5$)$_3$ |
| 2-Cl, 4-O-(4-Cl-C$_6$H$_4$) | —CH$_2$—CH$_2$— | HN(C$_2$H$_5$)$_3$ |
| 2-Cl, 4-O-(4-Cl-C$_6$H$_4$) | —CH$_2$—CH(C$_2$H$_5$)— | ½ Cu |
| 4-F | —CH$_2$—CH(C$_3$H$_7$-n)— | ½ Cu |
| 4-OCF$_3$ | —CH$_2$—CH(C$_3$H$_7$-n)— | ½ Cu |
| 2,4-F$_2$ | —CH$_2$—CH(C$_3$H$_7$-n)— | ½ Cu |
| 2-OCHF$_2$ | —CH$_2$—CH(C$_3$H$_7$-n)— | ½ Cu |
| 2-Cl, 4-O-(4-Cl-C$_6$H$_4$) | —(CH$_2$)$_3$— | ½ Cu |
| 2,4,6-Cl$_3$ | —CH$_2$—CH(C$_3$H$_7$-n)— | ½ Cu |
| — | —CH$_2$—CH(C$_3$H$_7$-n)— | ½ Cu |
| 2,4-F$_2$ | —CH$_2$—CH(CH$_3$)— | ½ Cu |

TABLE 9-continued (Ik)

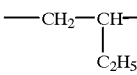

| $X^6_u$ | A | M |
|---|---|---|
| 2-Cl, 4-O-(4-Cl-C$_6$H$_4$) | —CH$_2$—CH(CH$_3$)— | ½ Cu |
| 2,4-Cl$_2$ | —CH(CH$_3$)—CH(CH$_3$)— | ½ Cu |
| 2-Cl, 4-O-(4-Cl-C$_6$H$_4$) | —CH(CH$_3$)—CH(CH$_3$)— | ½ Cu |
| 2,4-Cl$_2$ | —CH$_2$—CH(F)— | ½ Cu |
| 2-Cl, 4-O-(4-Cl-C$_6$H$_4$) | —CH$_2$—CH(C$_4$H$_9$-n)— | ½ Cu |
| 2,4-Cl$_2$ | —CH$_2$—CH(C$_2$H$_5$)— | ½ Cu |
| 2,4-Cl$_2$ | —CH$_2$—CH(C$_3$H$_7$-n)— | ½ Cu |
| 2,4-Cl$_2$ | —CH$_2$—CH(C$_3$H$_7$-n)— | ½ Cu |
| 2,4-Cl$_2$ | —CH$_2$—CH(C$_3$H$_7$-n)— | HN(C$_2$H$_5$)$_3$ |

TABLE 10

(Im)

Structure: phenyl with $X^7_v$ substituents, -CH($R^{16}$)-CH$_2$- linked to N of 1,2,4-triazole-5-thiolate $S^- M^+$

| $X^7_v$ | $R^{16}$ | M |
|---|---|---|
| 2,4-Cl$_2$ | —CH$_3$ | Na |
| 2,4-Cl$_2$ | —C$_2$H$_5$ | Na |
| 2,4-Cl$_2$ | —CH(CH$_3$)$_2$ | Na |
| 4-Cl | —C$_3$H$_7$-n | Na |
| 2,4-Cl$_2$ | —C$_4$H$_9$-n | Na |
| 2,4-Cl$_2$ | —CH(CH$_3$)—C$_2$H$_5$ | Na |
| 2,4-Cl$_2$ | —C(CH$_3$)$_3$ | Na |
| 2-Cl | —C$_3$H$_7$-n | Na |
| 2-OCF$_3$ | —C$_3$H$_7$-n | Na |
| 4-CF$_3$ | —C$_3$H$_7$-n | Na |
| 4-CH$_3$ | —C$_3$H$_7$-n | Na |
| 2,4,6-Cl$_3$ | —C$_3$H$_7$-n | Na |
| 2,4-Cl$_2$ | —(chloro-cyclopropyl) | Na |
| 4-F | —C$_3$H$_7$-n | Na |
| 2,4-Cl$_2$ | —(fluoro-cyclopropyl) | Na |
| 2,4-Cl$_2$ | —cyclopropyl | Na |
| 2,4-Cl$_2$ | —cyclopentyl | Na |
| 2,4-Cl$_2$ | —cyclohexyl | Na |
| 2,4-Cl$_2$ | —CH$_2$-cyclohexyl | Na |
| 2,4-Cl$_2$ | —CH(CH$_3$)-cyclopropyl | Na |
| 2,4-Cl$_2$ | —(4-chlorophenyl) | Na |
| 2,4-Cl$_2$ | —(4-fluorophenyl) | Na |
| 2,4-Cl$_2$ | —CH$_2$-(4-chlorophenyl) | Na |
| 2,4-Cl$_2$ | —CH$_2$-(4-fluorophenyl) | Na |
| 2,4-Cl$_2$ | —CH$_2$—O—CF$_2$—CHF$_2$ | Na |
| 2,4-Cl$_2$ | —CH$_2$—O—CF$_2$—CH$_3$ | Na |
| 4-Cl | —CH$_2$—O—CF$_2$—CHF$_2$ | Na |
| 2,4-Cl$_2$ | —CH$_2$—O—CF$_3$ | Na |
| 4-F | —CH$_2$—O—CF$_2$—CHF$_2$ | Na |
| 2-Cl | —CH$_2$—O—CF$_2$—CHF$_2$ | Na |
| 2,4-Cl$_2$ | —CH$_3$ | HN(C$_2$H$_5$)$_3$ |
| 2,4-Cl$_2$ | —C$_2$H$_5$ | HN(C$_2$H$_5$)$_3$ |
| 2,4-Cl$_2$ | —CH(CH$_3$)$_2$ | HN(C$_2$H$_5$)$_3$ |
| 4-Cl | —C$_3$H$_7$-n | HN(C$_2$H$_5$)$_3$ |
| 2,4-Cl$_2$ | —C$_4$H$_9$-n | HN(C$_2$H$_5$)$_3$ |
| 2,4-Cl$_2$ | —CH(CH$_3$)—C$_2$H$_5$ | HN(C$_2$H$_5$)$_3$ |
| 2,4-Cl$_2$ | —C(CH$_3$)$_3$ | HN(C$_2$H$_5$)$_3$ |
| 2-Cl | —C$_3$H$_7$-n | HN(C$_2$H$_5$)$_3$ |
| 2-OCF$_3$ | —C$_3$H$_7$-n | HN(C$_2$H$_5$)$_3$ |
| 4-CF$_3$ | —C$_3$H$_7$-n | HN(C$_2$H$_5$)$_3$ |
| 4-CH$_3$ | —C$_3$H$_7$-n | HN(C$_2$H$_5$)$_3$ |
| 2,4,6-Cl$_3$ | —C$_3$H$_7$-n | HN(C$_2$H$_5$)$_3$ |
| 2,4-Cl$_2$ | —(chloro-cyclopropyl) | HN(C$_2$H$_5$)$_3$ |
| 4-F | —C$_3$H$_7$-n | HN(C$_2$H$_5$)$_3$ |
| 2,4-Cl$_2$ | —(fluoro-cyclopropyl) | HN(C$_2$H$_5$)$_3$ |
| 2,4-Cl$_2$ | —cyclopropyl | HN(C$_2$H$_5$)$_3$ |
| 2,4-Cl$_2$ | —cyclopentyl | HN(C$_2$H$_5$)$_3$ |
| 2,4-Cl$_2$ | —cyclohexyl | HN(C$_2$H$_5$)$_3$ |
| 2,4-Cl$_2$ | —CH$_2$-cyclohexyl | HN(C$_2$H$_5$)$_3$ |

TABLE 10-continued (Im)

[Structure: phenyl ring with $X^7_v$ substituents, connected via $CH(R^{16})CH_2$ to N of triazole ring bearing $S^\ominus M^\oplus$]

| $X^7_v$ | $R^{16}$ | M |
|---|---|---|
| 2,4-Cl$_2$ | —CH(CH$_3$)(cyclopropyl) | HN(C$_2$H$_5$)$_3$ |
| 2,4-Cl$_2$ | 4-Cl-phenyl | HN(C$_2$H$_5$)$_3$ |
| 2,4-Cl$_2$ | 4-F-phenyl | HN(C$_2$H$_5$)$_3$ |
| 2,4-Cl$_2$ | —CH$_2$-(4-Cl-phenyl) | HN(C$_2$H$_5$)$_3$ |
| 2,4-Cl$_2$ | —CH$_2$-(4-F-phenyl) | HN(C$_2$H$_5$)$_3$ |
| 2,4-Cl$_2$ | —CH$_2$—O—CF$_2$—CHF$_2$ | ½ Cu |
| 2,4-Cl$_2$ | —CH$_2$—O—CF$_2$—CH$_3$ | ½ Cu |
| 4-Cl | —CH$_2$—O—CF$_2$—CHF$_2$ | ½ Cu |
| 2,4-Cl$_2$ | —CH$_2$—O—CF$_3$ | ½ Cu |
| 4-F | —CH$_2$—O—CF$_2$—CHF$_2$ | ½ Cu |
| 2-Cl | —CH$_2$—O—CF$_2$—CHF$_2$ | ½ Cu |
| 2,4-Cl$_2$ | —CH$_2$—CF$_3$ | Na |
| 2,4-Cl$_2$ | —CF$_2$—CF$_3$ | Na |
| 2,4-Cl$_2$ | —C$_3$H$_7$-n | Na |
| 2,4-Cl$_2$ | —C$_3$H$_7$-n | ½ Cu |
| 2,4-Cl$_2$ | —C$_3$H$_7$-n | HN(C$_2$H$_5$)$_3$ |

TABLE 11

(In)

[Structure: phenyl ring with $X^8_w$ substituents, connected via $Y^4$—CH—C(=O)—$R^{17}$ to N of triazole ring bearing $S^\ominus M^\oplus$]

| $X^8_w$ | $R^{17}$ | M | $Y^4$ |
|---|---|---|---|
| 2,4-Cl$_2$ | phenyl | Na | O |
| 4-Cl | phenyl | Na | O |
| 4-Br | —C(CH$_3$)$_3$ | Na | O |
| — | —C(CH$_3$)$_3$ | Na | O |
| 4-C(CH$_3$)$_3$ | —C(CH$_3$)$_3$ | Na | O |
| 2-Cl | —C(CH$_3$)$_3$ | Na | O |
| 3-Cl | —C(CH$_3$)$_3$ | Na | O |
| 4-F | —C(CH$_3$)$_3$ | Na | O |
| 4-phenyl | —C(CH$_3$)$_3$ | Na | O |
| 2-phenyl | —C(CH$_3$)$_3$ | Na | O |
| 2,4-Cl$_2$ | —C(CH$_3$)$_3$ | Na | O |
| 2-CH$_3$, 4-Cl | —C(CH$_3$)$_3$ | Na | O |
| 3,4-(CH$_3$)$_2$ | —C(CH$_3$)$_3$ | Na | O |
| 2,4,5-Cl$_3$ | —C(CH$_3$)$_3$ | Na | O |
| 4-Cl | —CH$_3$ | Na | O |
| 4-Cl | —CH$_2$-phenyl | Na | O |
| 4-CF$_3$ | —C(CH$_3$)$_3$ | Na | O |
| 4-OCF$_3$ | —C(CH$_3$)$_3$ | Na | O |
| 2-OCHF$_2$ | —C(CH$_3$)$_3$ | Na | O |
| 4-OCH$_3$ | —C(CH$_3$)$_3$ | Na | O |
| 2,4-Cl$_2$ | phenyl | HN(C$_2$H$_5$)$_3$ | O |
| 4-Cl | phenyl | HN(C$_2$H$_5$)$_3$ | O |
| 4-Br | —C(CH$_3$)$_3$ | ½ Cu | O |
| — | —C(CH$_3$)$_3$ | ½ Cu | O |
| 4-C(CH$_3$)$_3$ | —C(CH$_3$)$_3$ | ½ Cu | O |
| 2-Cl | —C(CH$_3$)$_3$ | ½ Cu | O |
| 3-Cl | —C(CH$_3$)$_3$ | ½ Cu | O |
| 4-F | —C(CH$_3$)$_3$ | ½ Cu | O |
| 4-phenyl | —C(CH$_3$)$_3$ | HN(C$_2$H$_5$)$_3$ | O |

TABLE 11-continued (In) Structure: X⁸_w-substituted phenyl–Y⁴–CH(triazole-S⁻ M⁺)–C(=O)–R¹⁷

| $X^8_w$ | $R^{17}$ | M | $Y^4$ |
|---|---|---|---|
| 2-phenyl | —C(CH₃)₃ | HN(C₂H₅)₃ | O |
| 2,4-Cl₂ | —C(CH₃)₃ | ½ Cu | O |
| 2-CH₃, 4-Cl | —C(CH₃)₃ | ½ Cu | O |
| 3,4-(CH₃)₂ | —C(CH₃)₃ | ½ Cu | O |
| 2,4,5-Cl₃ | —C(CH₃)₃ | ½ Cu | O |
| 4-Cl | —CH₃ | ½ Cu | O |
| 4-Cl | —CH₂—phenyl | HN(C₂H₅)₃ | O |
| 4-CF₃ | —C(CH₃)₃ | ½ Cu | O |
| 4-OCF₃ | —C(CH₃)₃ | ½ Cu | O |
| 2-OCHF₂ | —C(CH₃)₃ | ½ Cu | O |
| 4-OCH₃ | —C(CH₃)₃ | ½ Cu | O |
| 4-Cl | —C(CH₃)₂CH₂F | Na | O |
| 4-Cl | —C(CH₂F)₂CH₃ | Na | O |
| 4-Cl | —C(CH₃)₂CH₂F | HN(C₂H₅)₃ | O |
| 4-Cl | —C(CH₂F)₂CH₃ | HN(C₂H₅)₃ | O |
| 2,4-Cl₂ | 4-methylphenyl | Na | CH₂ |
| 4-Cl | 4-methylphenyl | Na | CH₂ |
| 4-Br | —C(CH₃)₃ | Na | CH₂ |
| — | —C(CH₃)₃ | Na | CH₂ |
| 4-C(CH₃)₃ | —C(CH₃)₃ | Na | CH₂ |
| 2-Cl | —C(CH₃)₃ | Na | CH₂ |
| 3-Cl | —C(CH₃)₃ | Na | CH₂ |
| 4-F | —C(CH₃)₃ | Na | CH₂ |
| 4-phenyl | —C(CH₃)₃ | Na | CH₂ |
| 2-phenyl | —C(CH₃)₃ | Na | CH₂ |
| 2,4-Cl₂ | —C(CH₃)₃ | Na | CH₂ |
| 2-CH₃, 4-Cl | —C(CH₃)₃ | Na | CH₂ |
| 3,4-(CH₃)₂ | —C(CH₃)₃ | Na | CH₂ |
| 2,4,5-Cl₃ | —C(CH₃)₃ | Na | CH₂ |
| 4-Cl | —CH₃ | Na | CH₂ |
| 4-Cl | —CH₂—phenyl | Na | CH₂ |
| 4-CF₃ | —C(CH₃)₃ | Na | CH₂ |
| 4-OCF₃ | —C(CH₃)₃ | Na | CH₂ |
| 2-OCHF₂ | —C(CH₃)₃ | Na | CH₂ |
| 4-OCH₃ | —C(CH₃)₃ | Na | CH₂ |
| 2,4-Cl₂ | 4-methylphenyl | HN(C₂H₅)₃ | CH₂ |
| 4-Cl | 4-methylphenyl | HN(C₂H₅)₃ | CH₂ |
| 4-Br | —C(CH₃)₃ | ½ Cu | CH₂ |
| — | —C(CH₃)₃ | ½ Cu | CH₂ |
| 4-C(CH₃)₃ | —C(CH₃)₃ | ½ Cu | CH₂ |
| 2-Cl | —C(CH₃)₃ | ½ Cu | CH₂ |
| 3-Cl | —C(CH₃)₃ | ½ Cu | CH₂ |
| 4-F | —C(CH₃)₃ | ½ Cu | CH₂ |
| 4-phenyl | —C(CH₃)₃ | HN(C₂H₅)₃ | CH₂ |
| 2-phenyl | —C(CH₃)₃ | HN(C₂H₅)₃ | CH₂ |
| 2,4-Cl₂ | —C(CH₃)₃ | ½ Cu | CH₂ |
| 2-CH₃, 4-Cl | —C(CH₃)₃ | ½ Cu | CH₂ |
| 3,4-(CH₃)₂ | —C(CH₃)₃ | ½ Cu | CH₂ |
| 2,4,5-Cl₃ | —C(CH₃)₃ | ½ Cu | CH₂ |
| 4-Cl | —CH₃ | ½ Cu | CH₂ |

TABLE 11-continued (In)

$$\text{structure: } X^8_w\text{-phenyl-}Y^4\text{-CH(}C(=O)R^{17}\text{)-N(triazole-5-S}^-M^+\text{)}$$

| $X^8_w$ | $R^{17}$ | M | $Y^4$ |
|---|---|---|---|
| 4-Cl | —CH₂—C₆H₅ (benzyl) | HN(C₂H₅)₃ | CH₂ |
| 4-CF₃ | —C(CH₃)₃ | ½ Cu | CH₂ |
| 4-OCF₃ | —C(CH₃)₃ | ½ Cu | CH₂ |
| 2-OCHF₂ | —C(CH₃)₃ | ½ Cu | CH₂ |
| 4-OCH₃ | —C(CH₃)₃ | ½ Cu | CH₂ |
| 4-Cl | —C(CH₃)(CH₃)(CH₂F) | Na | CH₂ |
| 4-Cl | —C(CH₂F)(CH₃)(CH₂F) | Na | CH₂ |
| 4-Cl | —C(CH₃)(CH₃)(CH₂F) | HN(C₂H₅)₃ | CH₂ |
| 4-Cl | —C(CH₂F)(CH₃)(CH₂F) | HN(C₂H₅)₃ | CH₂ |
| 4-Cl | —C(CH₃)₃ | Na | O |
| 4-Cl | —C(CH₃)₃ | ½ Cu | O |
| 4-Cl | —C(CH₃)₃ | HN(C₂H₅)₃ | O |

TABLE 12

(Ip)

$$\text{structure: } X^9_z\text{-phenyl-C(CN)(R}^{18}\text{)-CH}_2\text{-N(triazole-5-S}^-M^+\text{)}$$

| $X^9_z$ | $R^{18}$ | M |
|---|---|---|
| 4-Cl | —C₄H₉-n | Na |
| 2-Cl | —C₄H₉-n | Na |
| 2,4-Cl₂ | —C₄H₉-n | Na |
| 4-Br | —C₄H₉-n | Na |
| 4-F | —C₄H₉-n | Na |
| 4-C(CH₃)₃ | —C₄H₉-n | Na |
| 4-C₆H₅ | —C₄H₉-n | Na |
| 4-Cl | —C(CH₃)₃ | Na |
| 2-Cl | —C(CH₃)₃ | Na |
| 2,4-Cl₂ | —C(CH₃)₃ | Na |

TABLE 12-continued (Ip)

| $X^9_z$ | $R^{18}$ | M |
|---|---|---|
| 2,4,6-Cl$_3$ | —C(CH$_3$)$_3$ | Na |
| 4-CF$_3$ | —C(CH$_3$)$_3$ | Na |
| 2-OCHF$_2$ | —C(CH$_3$)$_3$ | Na |
| 4-Cl | —C(CH$_3$)$_2$CH$_2$F | Na |
| 4-Cl | —C(CH$_3$)(CH$_2$F)$_2$ | Na |
| 4-Cl | —CH$_2$—C$_6$H$_4$—4-Cl | Na |
| 4-Cl | —CH(CH$_3$)—C$_6$H$_4$—4-Cl | Na |
| 4-Cl | —C$_6$H$_4$—4-Cl | Na |
| 4-Cl | —CH$_2$—CH$_2$—C$_6$H$_4$—4-Cl | Na |
| — | —CH$_2$—CH$_2$—C$_6$H$_4$—4-F | Na |
| 4-Cl | —C$_4$H$_9$-n | ½ Cu |
| 2-Cl | —C$_4$H$_9$-n | ½ Cu |
| 2,4-Cl$_2$ | —C$_4$H$_9$-n | ½ Cu |
| 4-Br | —C$_4$H$_9$-n | ½ Cu |
| 4-F | —C$_4$H$_9$-n | ½ Cu |
| 4-C(CH$_3$)$_3$ | —C$_4$H$_9$-n | ½ Cu |
| 4-C$_6$H$_5$ | —C$_4$H$_9$-n | HN(C$_2$H$_5$)$_3$ |
| 4-Cl | —C(CH$_3$)$_3$ | ½ Cu |
| 2-Cl | —C(CH$_3$)$_3$ | ½ Cu |
| 2,4-Cl$_2$ | —C(CH$_3$)$_3$ | ½ Cu |
| 2,4,6-Cl$_3$ | —C(CH$_3$)$_3$ | ½ Cu |
| 4-CF$_3$ | —C(CH$_3$)$_3$ | ½ Cu |
| 2-OCRF$_2$ | —C(CH$_3$)$_3$ | ½ Cu |

TABLE 12-continued (Ip)

[Structure: phenyl ring with X⁹_z substituent, connected to C bearing CN and R¹⁸ groups, with CH₂ linker to N of triazole ring (1,2,4-triazole) bearing S⁺M⁻ at 5-position]

| X⁹_z | R¹⁸ | M |
|---|---|---|
| 4-Cl | —C(CH₃)₂—CH₂F (C with two CH₃ and one CH₂F) | HN(C₂H₅)₃ |
| 4-Cl | —C(CH₂F)₂—CH₃ (C with two CH₂F and one CH₃) | HN(C₂H₅)₃ |
| 4-Cl | —CH₂—C₆H₄—Cl (4-Cl) | HN(C₂H₅)₃ |
| 4-Cl | —CH(CH₃)—C₆H₄—Cl (4-Cl) | HN(C₂H₅)₃ |
| 4-Cl | —C₆H₄—Cl (4-Cl) | HN(C₂H₅)₃ |
| 4-Cl | —CH₂—CH₂—C₆H₄—Cl (4-Cl) | HN(C₂H₅)₃ |
| — | —CH₂—CH₂—C₆H₄—Cl (4-Cl) | HN(C₂H₅)₃ |
| — | —CH₂—CH₂—C₆H₄—F (4-F) | HN(C₂H₅)₃ |
| — | —CH₂—CH₂—C₆H₄—Cl (4-Cl) | Na |
| — | —CH₂—CH₂—C₆H₄—Cl (4-Cl) | ½ Cu |

Using 2-(1-chloro-cyclopropyl)-1-(2-chlorophenyl)-3-(5-mercapto-1,2,4-triazol-1-yl)-propan-2-ol as starting material and sodium hydroxide as reaction component, the course of the process according to the invention (variant a) can be illustrated by the equation below.

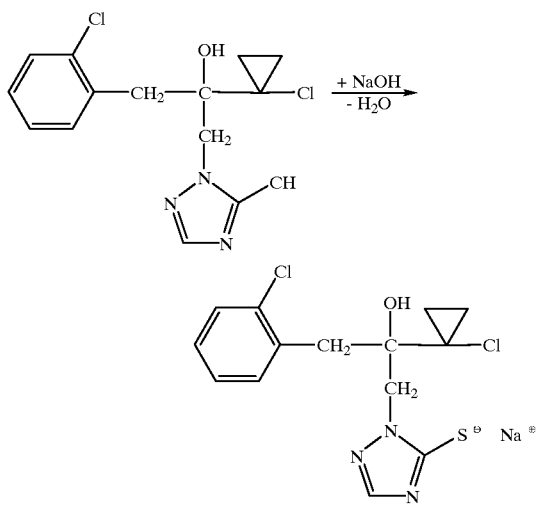

Using 2-(1-chloro-cyclopropyl)-1-(2-chloro-phenyl)-3-(5-mercapto-1,2,4-triazol-1-yl)-propan-2-ol as starting material and triethylamine as reaction component, the course of the process according to the invention (variant b) can be illustrated by the equation below.

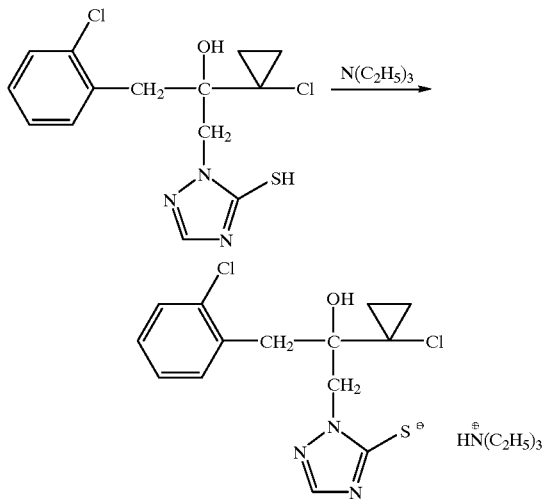

Using 2-(1-chloro-cyclopropyl)-1-(2-chloro-phenyl)-3-(5-mercapto-1,2,4-triazol-1-yl)-propan-2-ol as starting material and copper(II) acetate as reaction component, the course of the process according to the invention (variant c) can be illustrated by the equation below.

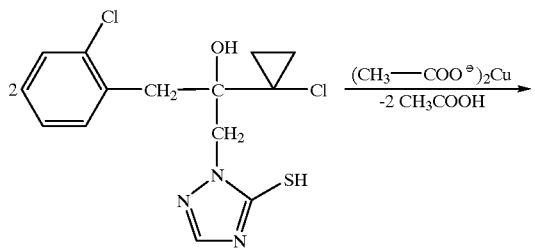

-continued

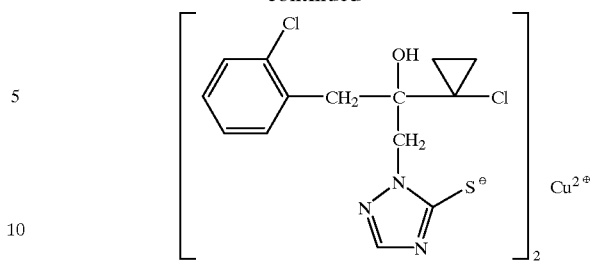

The formula (II) provides a general definition of the mercapto-triazoles required as starting materials for carrying out the process according to the invention. In this formula, $R^1$ preferably has those meanings which have already been mentioned in connection with the description of the substances of the formula (I) according to the invention as being preferred for this radical.

Some of the mercapto-triazoles of the formula (II) are known (cf. WO 87-06430). They can be prepared by reacting triazoles of the formula

in which $R^1$ is as defined above, either

α) successively with strong bases and sulphur in the presence of a diluent and then hydrolyzing with water, if appropriate in the presence of an acid, or β) with sulphur in the presence of a high-boiling diluent followed, if appropriate, by treatment with water and, if appropriate, with acid.

The formula (VI) provides a general definition of the triazoles required as starting materials for carrying out the process for preparing mercapto-triazoles of the formula (II). In this formula, $R^1$ preferably has those meanings which have already been mentioned in connection with the description of the substances of the formula (I) according to the invention as being preferred for this radical.

The triazoles of the formula (VI) are known or can be prepared by known methods (cf. EP-A 0 015 756, EP-A 0 040 345, EP-A 0 052 424, EP-A 0 061 835, EP-A 0 297 345, EP-A 0 094 564, EP-A 0 196 038, EP-A 0 267 778, EP-A 0 378 953, EP-A 0 068 813, EP-A 0 044 605, EP-A 0 069 442, EP-A 0 055 833, EP-A 0 301 393, DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786).

Suitable bases for carrying out the above process (α) for preparing mercaptotriazoles of the formula (II) are all strong alkali metal bases which are customary for reactions of this kind. Preference is given to using n-butyl-lithium, lithium diisopropyl-amide, sodium hydride, sodium amide and also potassium tert-butoxide in a mixture with tetramethylethylene-diamine (=TMEDA).

Suitable diluents for carrying out the above process (α) for preparing mercaptotriazoles of the formula (II) are all inert organic solvents which are customary for reactions of this kind. Preference is given to using ethers, such as tetrahydrofuran, dioxane, diethyl ether and 1,2-dimethoxyethane, furthermore liquid ammonia or else strongly polar solvents, such as dimethyl sulphoxide.

Both when carrying out the above process (α) and the process (β), sulphur is preferably employed in the form of a powder.

When carrying out the above process (α), water, if appropriate in the presence of an acid, is employed for the hydrolysis. Suitable acids are all inorganic or organic acids which are customary for reactions of this kind. Preference is given to using acetic acid, dilute sulphuric acid and dilute hydrochloric acid. However, it is also possible to carry out the hydrolysis using aqueous ammonium chloride solution.

When carrying out the above process (α), the reaction temperatures can be varied within a certain range. In general, the process is carried out at temperatures between –70° C. and +20° C., preferably between –70° C. and 0° C.

The above processes (α) and (β) are generally carried out under atmospheric pressure. However, it is also possible to carry out the processes under elevated or reduced pressure. Thus, in particular when carrying out the process (β), operation under elevated pressure is possible.

When carrying out the above process (α), generally 2 to 3 equivalents, preferably 2.0 to 2.5 equivalents, of a strong base and subsequently an equivalent amount or else an excess of sulphur are employed per mole of triazole of the formula (VI). The reaction can be carried out under an atmosphere of protective gas, for example under nitrogen or argon. Work-up is carried out by customary methods. In general, the reaction mixture is extracted with an organic solvent which is sparingly soluble in water, the combined organic phases are dried and concentrated and the residue that remains is purified, if appropriate, by recrystallization and/or chromatography.

Suitable diluents for carrying out the above process (β) are all high-boiling organic solvents which are customary for reactions of this kind. Preference is given to using amides, such as dimethylformamide and dimethylacetamide, furthermore heterocyclic compounds, such as N-methylpyrrolidone, and also ethers, such as diphenyl ether.

When carrying out the above process (β), a treatment, if appropriate, with water and, if appropriate, with acid may be carried out after the reaction. This treatment is carried out in the same manner as the hydrolysis in the practice of the process (α).

When carrying out the above process (β), the reaction temperatures may also be varied within a relatively wide range. In general, the process is carried out at temperatures between 150° C. and 300° C., preferably between 180° C. and 250° C.

When carrying out the above process (β), generally 1 to 5 mol, preferably 1.5 to 3 mol of sulphur are employed per mole of triazole of the formula (VI). Work-up is carried out by customary methods. In general, the reaction mixture is extracted with an organic solvent which is only sparingly soluble in water, the combined organic phases are dried and concentrated and the residue that remains is, if appropriate, freed of impurities that may be present using customary methods such as recrystallization or chromatography.

The formula (III) provides a general definition of the hydroxides required as reaction components for carrying out the process according to the invention according to variant (a). In this formula $M^1$ preferably represents a lithium, sodium or potassium cation, an equivalent of a magnesium or calcium cation or represents an ammonium cation of the formula

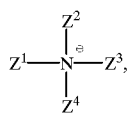

in which $Z^1$, $Z^2$, $Z^3$ and $Z^4$ each preferably have those meanings which have already been mentioned in connection with the description of the substances of the formula (I) according to the invention as being preferred for these substituents.

$M^1$ particularly preferably represents a lithium, sodium or potassium cation, an equivalent of a magnesium or calcium cation or represents an ammonium cation of the formula

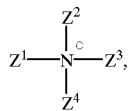

in which $Z^1$, $Z^2$, $Z^3$ and $Z^4$ each particularly preferably have those meanings which have already been mentioned in connection with the description of the substances of the formula (I) according to the invention as being particularly preferred for these substituents.

The hydroxides of the formula (III) are known or can be prepared by known methods.

Suitable diluents for carrying out the process according to the invention according to variant (a) are all customary inert organic solvents. Preference is given to using halogenated hydrocarbons, such as dichloromethane, furthermore alcohols, such as methanol, ethanol, n-propanol or n-butanol, and moreover strongly polar solvents, such as dimethylformamide or dimethyl sulphoxide.

When carrying out the process according to the invention according to variant (a), the reaction temperatures can be varied within a relatively wide range. In general, the process is carried out at temperatures between –30° C. and +100° C., preferably at temperatures between 0° C. and +60° C.

When carrying out the process according to the invention both according to variant (a) and according to variants (b) or (c), the process is generally carried out under atmospheric pressure. However, it is also possible to operate under elevated or reduced pressure.

When carrying out the process according to the invention according to variant (a), generally an equivalent or else an excess of hydroxide of the formula (III) is employed per mole of mercapto-triazole of the formula (II). Work-up is carried out by customary methods. In general, the reaction mixture is concentrated under reduced pressure and the residue is, if appropriate, washed and dried. The resulting product can, if appropriate, be freed of any impurities that may still be present using customary methods.

The formula (IV) provides a general definition of the amines required as reaction components for carrying out the process according to the invention according to variant (b). In this formula, $Z^2$, $Z^3$ and $Z^4$ each preferably have those meanings which have already been mentioned in connection with the description of the substances of the formula (I) according to the invention as being preferred for these substituents.

$Z^2$ particularly preferably represents hydrogen or straight-chain or branched alkyl having 1 to 6 carbon atoms, $Z^3$ particularly preferably represents hydrogen, straight-chain or branched alkyl having 1 to 6 carbon atoms, benzyl or phenyl, and $Z^4$ particularly preferably represents straight-chain or branched alkyl having 1 to 18 carbon atoms, benzyl or phenyl.

The amines of the formula (IV) are known or can be prepared by known methods.

Suitable diluents for carrying out the process according to the invention according to variant (b) are all customary inert organic solvents. Preference is given to using aromatic hydrocarbons, such as toluene, xylene or decalin, furthermore halogenated hydrocarbons, such as dichloromethane, chloroform, tetrachloromethane, dichloroethane or trichloroethane, also ethers, such as diethyl ether, diisopropyl ether, methyl tert-butyl ether, methyl tert-amyl ether, dioxane or tetrahydrofuran, and moreover nitriles, such as acetonitrile, propionitrile, n- or isobutyronitrile.

When carrying out the process according to the invention according to variant (b), the reaction temperatures may also be varied within a certain range. In general, the process is carried out at temperatures between 0° C. and 100° C., preferably between 10° C. and 60° C.

When carrying out the process according to the invention according to variant (b), generally an equivalent amount or else an excess of amine of the formula (IV) is employed per mole of mercapto-triazole of the formula (II). Work-up is carried out by customary methods. In general, the reaction mixture is concentrated under reduced pressure and the residue is, if appropriate, washed and dried. The resulting product can be freed of any impurities that may still be present using customary methods. The formula (V) provides a general definition of the acetates required as reaction components for carrying out the process according to the invention according to variant (c). In this formula, $M^2$ preferably represents an equivalent of a copper, zinc, iron or nickel cation.

The acetates of the formula (V) are known.

Suitable diluents for carrying out the process according to the invention according to variant (c) are again all inert organic solvents which are customary for reactions of this kind. Preference is given to using those solvents which have already been mentioned in connection with the description of process variant (a) as being preferred.

When carrying out the process according to the invention according to variant (c), the reaction temperatures can again be varied within a certain range. In general, the process is carried out at temperatures between 0° C. and 100° C., preferably between 10° C. and 60° C.

When carrying out the process according to the invention according to variant (c), in general an equivalent amount or else an excess of acetate of the formula (V) is employed per mole of mercapto-triazole of the formula (II). Work-up is carried out by customary methods. In general, the reaction mixture is concentrated under reduced pressure and the residue is, if appropriate, washed and dried. The resulting product can be freed from any impurities that may still be present using customary methods.

The active compounds according to the invention have a powerful microbicidal action and can be employed for controlling undesirable microorganisms, such as fungi and bacteria, in crop protection and in the protection of materials.

Fungicides in crop protection are employed for controlling Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*

Pseudomonas species, such as *Pseudomonas lachrymans;*

Erwinia species, such as *Erwinia amylovora;*

Pythium species, such as *Pythium ultimum;*

Phytophthora species, such as *Phytophthora infestans;*

Pseudoperonospora species, such as *Pseudoperonospora humuli* or *Pseudoperonospora cubensis;*

Plasmopara species, such as *Plasmopara viticola;*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *P. graminea*

(conidia form: Drechslera, syn: Helminthosporium);

Cochliobolus species, such as *Cochliobolus sativus*

(conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as *Alternaria brassicae* and

Pseudocercosporella species, such as *Pseudocercosporella herpotrichoides.*

The good toleration, by plants, of the active compounds, at the concentrations required for controlling plant diseases, permits treatment of above-ground parts of plants, of vegetative propagation stock and seeds, and of the soil.

The active compounds according to the invention are particularly suitable for controlling *Pyricularia oryzae* and *Pellicularia sasakii* in rice and for controlling cereal diseases, such as Pseudocerosporella, Erysiphe species and Fusarium species. Moreover, the substances according to the invention can be employed very successfully against Venturia and Sphaerotheca. In addition, they also have a very good in-vitro action.

In the protection of materials the substances of the invention can be used to protect industrial materials against infestation and destruction by undesirable microorganisms.

The term industrial materials in the present context refers to nonliving materials which have been prepared for use in industry. Examples can be industrial materials which are to be protected by novel active compounds against microbial alteration or destruction, adhesives, sizes, paper and card, textiles, leather, wood, coating compositions and plastics articles, cooling lubricants and other materials which can be infested or decomposed by microorganisms. In the context of the materials to be protected mention may also be made of parts of production plants, for example cooling water circuits, which may be adversely affected by reproduction of microorganisms. Preferred industrial materials in the context of the present invention are adhesives, sizes, papers and cards, leather, wood, coating compositions, cooling lubricants and heat transfer fluids, especially wood.

Examples of microorganisms which can bring about degradation or an alteration in the industrial materials are bacteria, fungi, yeasts, algae and slime organisms. The active compounds according to the invention preferably act against fungi, especially mould fungi, wood-discolouring and wood-destroying fungi (Basidiomycetes) and also against slime organisms and algae.

By way of example, mention may be made of the following genera:

Altemaria, such as *Altemaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on their respective physical and/or chemical properties, the active compounds can be converted into customary formulations, such as solutions, emulsions, suspensions, powders, foams, pastes, granules, aerosols, very fine capsules in polymeric substances and in coating compositions for seed, and also ULV cold-mist and warm-mist formulations.

These formulations are prepared in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. If the extender used is water, it is also possible to employ for example organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersing agents there are suitable: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compounds according to the invention, when used in crop protection, can be used as such or, in formulations, also as a mixture with known fungicides, bactericides, acaricides, nematicides or insecticides, for example so as to widen the spectrum of action or to prevent the build up of resistance. In many cases, this results in synergistic effects, i.e. the activity of the mixture exceeds the activity of the individual components.

Suitable components for the mixtures are, for example, the following substances:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaiicides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cyperrnethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators, is also possible.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the concentrations of active substance in use forms can be varied within a relatively large range: They are in general between 1 and 0.0001% by weight, preferably between 0.5 and 0.001% by weight. In the treatment of seed, amounts of active substance of from 0.001 to 50 g per kilogram of seed, preferably from 0.01 to 10 g, are generally required.

In the case of the treatment of soil, active-substance concentrations of from 0.00001 to 0.1% by weight, preferably from 0.0001 to 0.02% by weight, are required at the site of action.

The compositions used for protecting industrial materials comprise the active substances in an amount of in general from 1 to 95%, preferably from 10 to 75%.

The concentrations in which the novel active substances are applied depend on the nature and on the incidence of the microorganisms to be controlled and on the composition of the material to be protected. The optimum amount for use can be determined by means of test series. In general, the use concentrations are in the range from 0.001 to 5% by weight, preferably from 0.05 to 1.0% by weight, based on the material to be protected.

The effectiveness and the spectrum of action of the active substances to be used in the protection of materials in accordance with the invention and of the compositions, concentrates or, very generally, formulations which can be prepared therefrom can be increased by adding, if desired, further antimicrobially active compounds, fungicides, bactericides, herbicides, insecticides or other active substances to increase the spectrum of action or to achieve particular effects, for example additional protection against insects. These mixtures may possess a broader spectrum of action than the compounds according to the invention.

Preparation and use of the substances according to the invention can be seen from the examples which follow.

PREPARATION EXAMPLES

Example 1

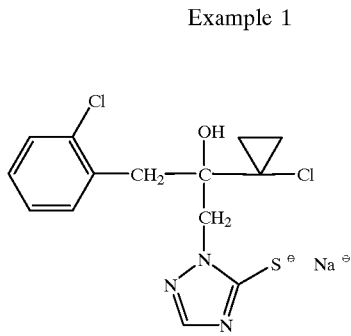
(I-1)

At room temperature, a solution of 50 g (0.146 mol) of 2-(1-chloro-cyclopropyl)-1-(2-chlorophenyl)-3-(5-mercapto-1,2,4-triazol-1-yl)-propan-2-ol in 730 ml of absolute ethanol is admixed dropwise with stirring with a solution of 5.84 g (0.146 mol) of sodium hydroxide in 365 ml of absolute ethanol. After the addition has ended, the reaction mixture is concentrated under reduced pressure. The residue that remains is washed with n-hexane and dried. In this manner, 52.8 g (98% of theory) of the sodium salt of 2-(1-chloro-cyclopropyl)-1-(2-chlorophenyl)-3-(5-mercapto-1,2,4-triazol-1-yl)-propan-2-ol are obtained in the form of a solid substance of melting point 268–270° C.

Example 2

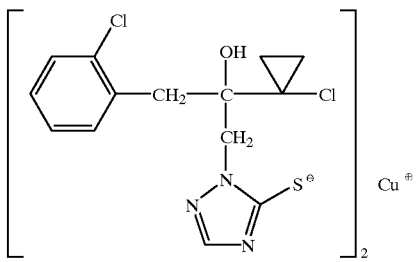
(I-2)

At room temperature, a solution of 1.72 g (5 mmol) of 2-(1-chloro-cyclopropyl)-1-(2-chlorophenyl)-3-(5-mercapto-1,2,4-triazol-1-yl)-propan-2-ol in 20 ml of absolute methanol is admixed dropwise with stirring with a solution of 0.5 g (2.5 mmol) of copper(II) acetate in 5 ml of water. After the addition has ended, the reaction mixture is heated with stirring at 50° C. for 2 hours. The reaction mixture is subsequently concentrated under reduced pressure. The residue that remains is dried under high vacuum. In this manner, 1.9 g (100% of theory) of the copper salt of 2-(1-chloro-cyclopropyl)-1-(2-chlorophenyl)-3-(5-mercapto-1,2,4-triazol-1-yl)-propan-2-ol are obtained in the form of a solid substance of melting point 107–109° C.

Example 3

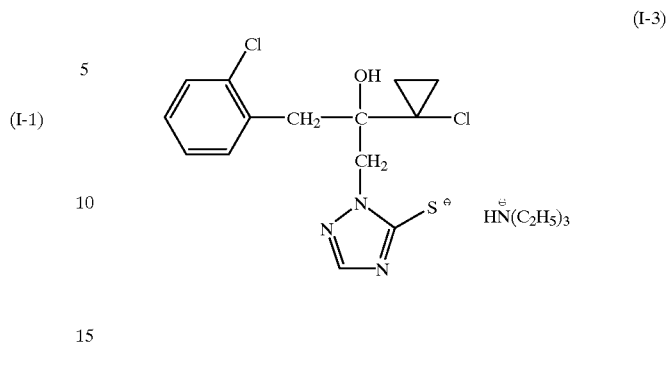
(I-3)

At room temperature, a solution of 1.72 g (5 mmol) of 2-(1-chlorocyclopropyl)-1-(2-chlorophenyl)-3-(5-mercapto-1,2,4-triazol-1-yl)-propan-2-ol in 20 ml of dichloromethane is admixed dropwise with stirring with 0.5 g (5 mmol) of triethylamine. After the addition has ended, the reaction mixture is initially stirred for a further hour at 20° C. and then concentrated under reduced pressure. The residue that remains is dried under high vacuum. In this manner, 2.2 g (99% of theory) of the triethylammonium salt of 2-(1-chloro-cyclopropyl)-1-(2-chlorophenyl)-3-(5-mercapto-1,2,5-triazol-1-yl)-propan-2-ol are obtained in the form of an oil.

$^1$H NMR spectrum (200 MHz; CDCl$_3$; TMS): δ=0.6–0.9 (m, 4H); 1.3 (t, 9H); 3.2 (q, 6H); 3.35 (AB, 2H); 4.65 (AB, 2H); 5.9 (s, OH); 7.1–7.65 (m, 4H); 7.6 (s, 1H); 11.7 (NH) ppm.

The compounds listed in the Examples below are also prepared by the method given in Example 3.

Example 4

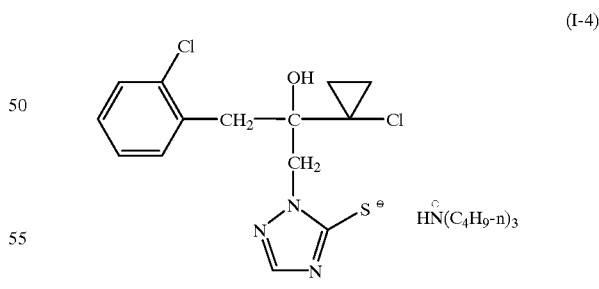
(I-4)

Oil $^1$H NMR spectrum (200 MHz; CDCl$_3$, TMS): δ=0.6–1.0 (m, 4H); 0.95 (t, 9H); 1.3–1.7 (m, 12H), 3.0 (m, 6H); 3.15 (d, 1H); 3.55 (d, 1H); 4.55 (d, 1H); 4.75 (d, 1H); 6.05 (OH); 7.1–7.65 (m, 4H); 7.55 (s, 1H); 11.6 (NH) ppm.

Example 5

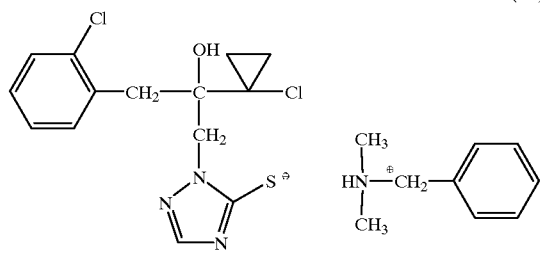

Melting point: 86° C.

Example 6

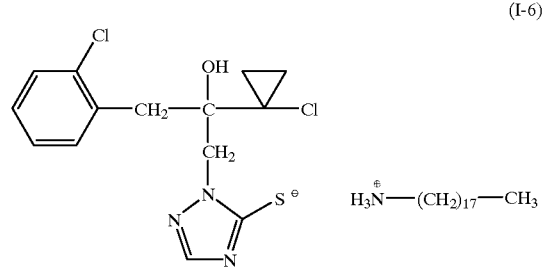

Oil $^1$H NMR spectrum (400 MHz; CDCl$_3$, TMS): δ=0.7–0.9 (m, 4H); 0.9 (t, 9H); 1.25 (m, 30H); 1.5 (m, 3H); 2.8 (t, 2H); 3.2 (d, 1H); 3.5 (d, $_1$H); 4.5 (d, $_1$H); 4.75 (d, $_1$H); 6.2 (OH); 7.5–7.55 (m, 4H); 7.65 (s, 1H) ppm.

Example 7

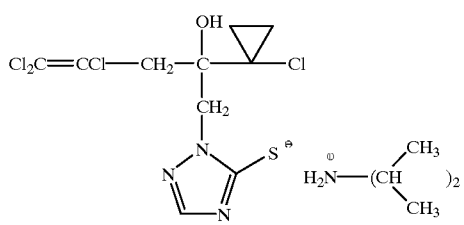

Melting point: 132–135° C.

Example 8

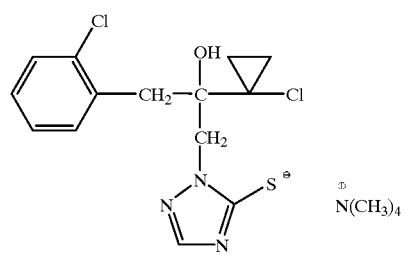

At room temperature, 1.72 g (5 mmol) of 2-(1-chloro-cyclopropyl)-1-(2-chlorophenyl)-3-(5-mercapto-1,2,4-triazol-1-yl)-propan-2-ol and 0.91 g (5 mmol) of tetramethylammonium hydroxide in the form of the pentahydrate are dissolved with stirring in 30 ml of dichloromethane. The reaction mixture is subsequently concentrated under reduced pressure. The residue that remains is dried under high vacuum. In this manner, 2.1 g (100% of theory) of the tetramethylammonium salt of 2-(1-chloro-cyclopropyl)-1-(2-chlorophenyl)-3-(5-mercapto-1,2,4-triazol-1-yl)-propan-2-ol are obtained in the form of a solid substance of melting point 155° C.

Preparation of starting materials:

Example 9

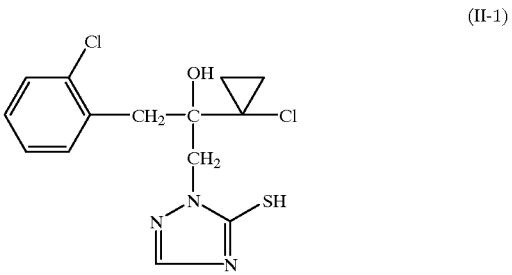

Variant α:

At −20° C., a mixture of 3.12 g (10 mmol) of 2-(1-chloro-cyclopropyl)-1-(2-chlorophenyl)-3-(1,2,4-triazol-1-yl)-propan-2-ol and 45 ml of absolute tetrahydrofuran is admixed with 8.4 ml (21 mmol) of n-butyllithium in hexane and stirred at 0° C. for 30 minutes. The reaction mixture is then cooled to −70° C., admixed with 0.32 g (10 mmol) of sulphur powder and stirred at −70° C. for 30 minutes. The mixture is warmed to −10° C., admixed with ice-water and adjusted to pH 5 by addition of dilute sulphuric acid. The mixture is extracted repeatedly with ethyl acetate and the combined organic phases are dried over sodium sulphate and concentrated under reduced pressure. In this manner, 3.2 g (93% of theory) of 2-(1-chloro-cyclopropyl)-1-(2-chlorophenyl)-3-(5-mercapto-1,2,4-triazol-1-yl)-propan-2-ol are obtained in the form of a solid substance which, after recrystallization, melts at 138–139° C.

Variant β:

A mixture of 3.12 g (10 mmol) of 2-(1-chloro-cyclopropyl)-1-(2-chloro-phenyl)-3-(1,2,4-triazol-1-yl)-propan-2-ol, 0.96 g (30 mmol) of sulphur powder and 20 ml of absolute N-methyl-pyrrolidone is heated with stirring at 200° C. for 44 hours. The reaction mixture is subsequently concentrated under reduced pressure (0.2 mbar). The resulting crude product (3.1 g) is recrystallized from toluene. In this manner, 0.7 g (20% of theory) of 2-(1-chloro-cyclopropyl)-1-(2-chlorophenyl)-3-(5-mercapto-1,2,4-triazol-1-yl)-propan-2-ol is obtained in the form of a solid substance of melting point 138–139° C.

Example 10

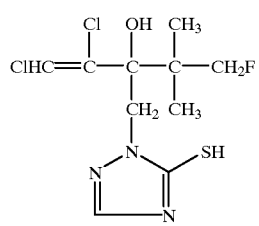
(II-2)

At −70° C., a mixture of 1.41 g (5 mmol) of 1,2-dichloro-4,4-dimethyl-5-fluoro-3-hydroxy-3-[(1,2,4-triazol-1-yl)-methyl]-1-pentene and 25 ml of absolute tetrahydrofuran is admixed with 4 ml (10 mmol) of n-butyl-lithium in hexane and stirred at −70° C. for one hour. The reaction mixture is then admixed with 0.19 g (6 mmol) of sulphur powder and stirred at −70° C. for 4 hours. The mixture is subsequently hydrolyzed by adding 1 ml of methanol and 1 ml of acetic acid at −70° C. The reaction mixture is initially diluted with ethyl acetate and then extracted repeatedly with saturated aqueous ammonium chloride solution. The organic phase is dried over sodium sulphate and concentrated under reduced pressure. The resulting crude product (1.7 g) is purified by silica gel chromatography using a mixture of petroleum ether and ethyl acetate=1:1 as eluent. In this manner, 0.5 g (32% of theory) of 1,2-dichloro-4,4-dimethyl-5-fluoro-3-hydroxy-3-[(5-mercapto-1,2,4-triazol-1-yl)-methyl]-1-pentene is obtained in the form of a solid substance of melting point 162–164° C.

The compounds listed in Table 13 below are also prepared by the methods given in Examples 9 and 10.

TABLE 13

(II-b)

| Ex. No. | Comp. No. | $R^2$ | $R^3$ | Physical constant |
|---|---|---|---|---|
| 11 | (II-3) | —CCl=CHCl | —C(CH$_3$)$_3$ | mp. 168–169° C. |
| 12 | (II-4) | 2-OCHF$_2$-phenyl | cyclopropyl-Cl | GC/MS (Cl):376 (M + H$^+$) |
| 13 | (II-5) | 4-F-phenyl | cyclopropyl-CN | mp. 163–164° C. |
| 14 | (II-6) | —CH$_2$—O—(4-Cl-phenyl) | —C(CH$_3$)$_3$ | mp. 127° C. |
| 15 | (II-7) | 4-Cl-phenyl | —C(CH$_3$)$_2$—CH=N—OCH$_3$ | Oil |
| 16 | (II-8) | 2-F-phenyl-C(=CH$_2$)— | cyclopropyl-Cl | GC/MS (Cl):340 (M + H$^+$) |
| 17 | (II-9) | 4-Cl-phenyl | —C(CH$_3$)$_2$—O—(4-Cl-phenyl) | GC/MS (Cl):424 (M + H$^+$) |

TABLE 13-continued (II-b)

Structure: R²–C(OH)(R³)–CH₂–N(triazole-SH)

| Ex. No. | Comp. No. | R² | R³ | Physical constant |
|---|---|---|---|---|
| 18 | (II-10) | —C₆H₄—Cl (4-Cl-phenyl) | cyclopropyl-F | mp. 168° C. |
| 19 | (II-11) | —C₆H₄—F (4-F-phenyl) | cyclopropyl-Cl | GC/MS (CI):314 (M + H⁺) |
| 20 | (II-12) | —CH₂—C₆H₄—F (2-F-benzyl) | —C(CH₂F)(CH₃)(CH₂F) | GC/MS (CI):346 (M + H⁺) |
| 21 | (II-13) | —CH₂—C₆H₄—Cl (2-Cl-benzyl) | cyclopropyl-F | mp. 115–118° C. |
| 22 | (II-14) | —CH₂—CH₂—C₆H₄—Cl (4-Cl-phenethyl) | —C(CH₃)₃ | GC/MS (CI):340 (M + H⁺) |
| 23 | (II-15) | 2-F-phenyl | —C₆H₄—F (4-F-phenyl) | GC/MS (CI):334 (M + H⁺) |
| 24 | (II-16) | 2,4-diCl-phenyl | —C₄H₉-n | *) |

*)The compound is characterized by the following signals in the ¹H NMR spectrum (400 MHz, CDCl₃/TMS):
δ = 0.8(t, 3H); 0.85(m, 2H); 1.25(m, 2H); 1.8(m, 1H); 2.55(m, 1H); 4.6(OH); 4.9(AB, 2H); 7.2(dd, 1H); 7.35 (d, 1H); 7.7(s, 1H); 7.75(d, 1H); 12.3(5H) ppm.

Example 25

(II-17)

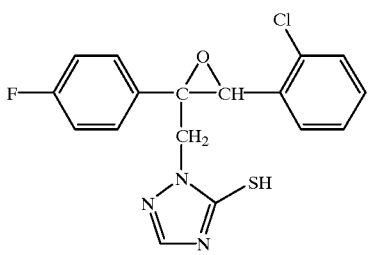

At −70° C., a mixture of 1.3 g (4 mmol) of 3-(2-chloro-phenyl)-2-(4-fluoro-phenyl)-2-(1,2,4-triazol-1-yl-methyl)-oxirane (Z form) and 25 ml of absolute tetrahydrofuran is admixed with 2.0 ml (5 mmol) of n-butyl-lithium in hexane and stirred at −70° C. for 1 hour. The reaction mixture is then admixed with 0.16 g (5 mmol) of sulphur powder and stirred at −70° C. for 4 hours. At −70° C., 1 ml of methanol and 1 ml of acetic acid are subsequently added simultaneously, dropwise and with stirring. The resulting mixture is diluted with dichloromethane and extracted repeatedly with saturated aqueous ammonium chloride solution. The organic phase is dried over sodium sulphate and then concentrated under reduced pressure. The resulting crude product (1.9 g), which, according to GC contains 51.0% of the desired product in addition to 20.7% of starting material, is recrystallized from toluene. In this manner, 0.8 g (55% of theory) of 3-(2-chlorophenyl)-2-(4-fluoro-phenyl)-2-(5-mercapto-1,2,4-triazol-1-yl-methyl)oxirane (Z form) is obtained as a solid substance of melting point 179 to 180° C.

$^1$H NMR spectrum (200 MHz; CDCl$_3$, TMS): δ=3.7 (d, J=15 Hz, 1H); 4.1 (s, 1H); 5.15 (d, J=15 Hz, 1H); 6.95–7.6 (m, 8H); 7.65 (s, 1H); 11.0 (SH) ppm.

GC/MS (ci): 362 (M+H$^+$)

Example 26

(II-18)

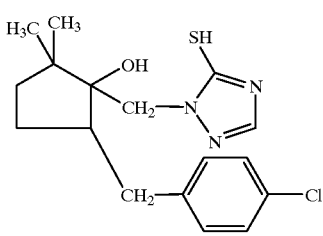

At −20° C., a mixture of 1.6 g (5 mmol) of 5-(4-chlorobenzyl)-2,2-dimethyl-1-(1,2,4-triazol-1-yl-methyl)-cyclopentan-1-ol (Z form) and 30 ml of absolute tetrahydrofuran is admixed with 4 ml (10 mmol) of n-butyl-lithium in hexane and stirred at 0° C. for another 30 minutes. The reaction mixture is subsequently cooled to −70° C., admixed with stirring with 0.19 g (6 mmol) of sulphur powder and then stirred at −70° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (2.0 g) is recrystallized from toluene. In this manner, 1.1 g (63% of theory) of 5-(4-chloro-benzyl)-2,2-dimethyl-1-(5-mercapto-1,2,4-triazol-1-yl-methyl)-cyclopentan-1-ol (Z form) are obtained as a solid substance of melting point 179 to 180° C.

GC/MS (ci): 352 (M+H$^+$)

Example 27

(II-19)

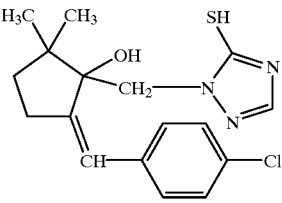

At −20° C., a mixture of 1.59 g (5 mmol) of 2-(4-chloro-benzylidene)-5,5-dimethyl-1-(1,2,4-triazol-1-yl-methyl)-cyclopentan-1-ol and 30 ml of absolute tetrahydrofuran is admixed with 4.4 ml (11 mmol) of n-butyl-lithium in hexane and stirred at 0° C. for another 30 minutes. The reaction mixture is subsequently cooled to −70° C., admixed with stirring with 0.19 g (6 mmol) of sulphur powder and then stirred at −70° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.9 g) is chromatographed over silica gel using ethyl acetate. In this manner, 0.8 g (46% of theory) of 2-(4-chloro-benzylidene)-5,5-dimethyl-1-(5-mercapto-1,2,4-triazol-1-yl-methyl)-cyclopentan-1-ol is obtained.

$^1$H NMR spectrum (200 MHz; CDCl$_3$, TMS): δ=0.9 (s,3H); 1.15 (s,3H); 1.6–1.95 (m,2H); 2.4–3.0 (m,2H); 4.25 (d,1H); 4.55 (d,1H); 5.9 (m,1H); 7.1–7.3 (m,4H); 7.6 (s,1H) ppm

Example 28

(II-20)

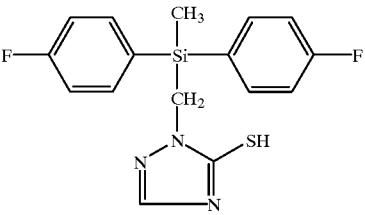

At 0° C., a mixture of 1.58 g (5 mmol) of bis-(4-fluoro-phenyl)-methyl-(1,2,4-triazol-1-yl-methyl)-silane and 30 ml of absolute tetrahydrofuran is admixed with 2 ml (5 mmol) of n-butyl-lithium in hexane and stirred at 0° C. for 1 hour. The reaction mixture is subsequently cooled to −70° C., admixed with stirring with 0.16 g (5 mmol) of sulphur powder and then stirred at −70° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.8 g) is purified by silica gel chromatography using a mixture of petroleum ether and ethyl acetate=1:1 as eluent. In this manner, 0.6 g (35% of theory) of bis-(4-fluoro-phenyl)-methyl-(5-mercapto-1,2,4-triazol-1-yl-methyl)-silane is obtained.

$^1$H NMR spectrum (200 MHz; CDCl$_3$, TMS): δ=0.7 (s, 3H); 4.2 (s, 2H); 7.05 (m, 4H); 7.55 (m, 5H); 13.1 (s, 1H) ppm

GC/MS(EI): 347 (M$^+$, 20%)

Example 29

(II-21)

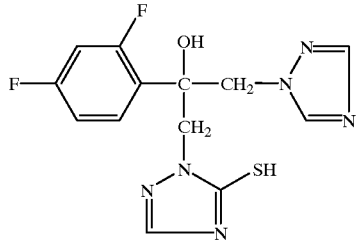

At −20° C., a mixture of 1.53 g (5 mmol) of 2-(2,4-difluoro-phenyl)-1,3-bis-(1,2,4-triazol-1-yl)-propan-2-ol and 30 ml of absolute tetrahydrofuran is admixed with 4.4 ml (11 mmol) of n-butyl-lithium in hexane and stirred at 0° C. for another 30 minutes. The reaction mixture is subsequently cooled to −70° C., admixed with stirring with 0.19 g (6 mmol) of sulphur powder and then stirred at −70° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (2.3 g) is purified by silica gel chromatography using a mixture of ethyl acetate and ethanol=9:1 as eluent. In this manner, 1.0 g (59% of theory) of 2-(2,4-difluoro-phenyl)-1-(5-mercapto-1,2,4-triazol-1-yl)-3-(1,2,4-triazol-1-yl)-propan-2-ol is obtained in the form of a solid substance of melting point 187° C.

GC/MS(ci): 339 (M+H$^+$)

Example 30

(II-22)

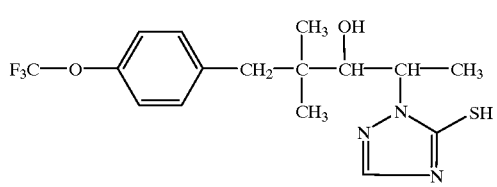

At −20° C., a mixture of 1.72 g (5 mmol) of 2,2-dimethyl-3-hydroxy-4-(1,2,4-triazol-1-yl)-1-(4-trifluoromethoxy-phenyl)-pentane and 30 ml of absolute tetrahydrofuran is admixed with 4.4 ml (11 mmol) of n-butyl-lithium in hexane and stirred at 0° C. for another 30 minutes. The reaction mixture is subsequently cooled to −70° C., admixed with stirring with 0.19 g (6 mmol) of sulphur powder and then stirred at −70° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (2.2 g) is purified by silica gel chromatography using a mixture of petroleum ether and ethyl acetate=1:1 as eluent. In this manner, 1.4 g (75% of theory) of 2,2-dimethyl-3-hydroxy-4-(5-mercapto-1,2,4-triazol-1-yl)-1-(4-trifluoromethoxy-phenyl)-pentane are obtained in the form of a solid substance of melting point 125 to 126° C.

GC/MS(ci): 376 (M+H$^+$)

Example 31

(II-23)

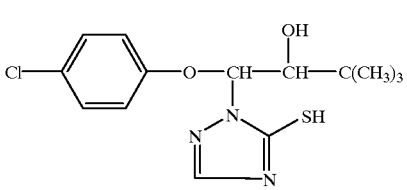

At −20° C., a mixture of 1.48 g (5 mmol) of 1-(4-chloro-phenoxy)-1-(1,2,4-triazol-1-yl)-3,3-dimethyl-butan-2-ol and 30 ml of absolute tetrahydrofuran is admixed with 4 ml (10 mmol) of n-butyl-lithium in hexane and stirred at −20° C. for another 30 minutes. At −20° C., the reaction mixture is subsequently admixed with stirring with 0.19 g (6 mmol) of sulphur powder and then stirred at −20° C. for 1 hour and then at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.9 g) is purified by silica gel chromatography using a mixture of petroleum ether and ethyl acetate=1:1 as eluent. In this manner, 0.7 g (43% of theory) of 1-(4-chlorophenoxy)-1-(5-mercapto-1,2,4-triazol-1-yl)-3,3-dimethyl-butan-2-ol is obtained in the form of a solid substance of melting point 193 to 194° C.

MS(ci): 328 (M +H$^+$)

Example 32

(II-24)

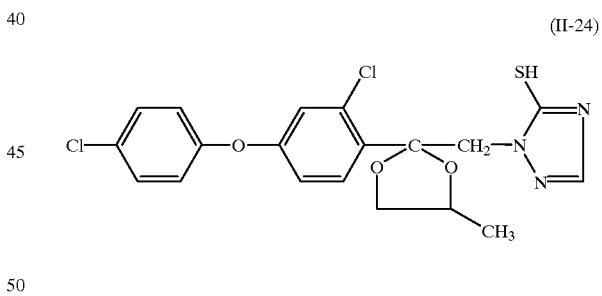

A mixture of 2.0 g (5 mmol) of 2-[2-chloro-4-(4-chlorophenoxy)-phenyl]-2-(1,2,4-triazol-1-yl-methyl)-4-methyl-1,3-dioxolane, 0.32 g (10 mmol) of sulphur powder and 10 ml of absolute N-methylpyrrolidone is heated with stirring at 200° C. for 22 hours. The reaction mixture is subsequently concentrated under reduced pressure (0.2 mbar). The residue that remains is admixed with ethyl acetate, and the resulting mixture is extracted repeatedly with saturated aqueous ammonium chloride solution. The organic phase is dried over sodium sulphate and then concentrated under reduced pressure. The resulting crude product (1.8 g) is purified by silica gel chromatography using a mixture of petroleum ether and ethyl acetate=1:1 as eluent. In this manner, 0.9 g (41% of theory) of 2-[2-chloro-4-(4-chloro-phenoxy)-phenyl]-2-[(5-mercapto-1,2,4-triazol-1-yl)-methyl]4-methyl-1,3-dioxolane is obtained in the form of an isomer mixture.

MS(ci): 438 (M +H+, 100%)

Example 33

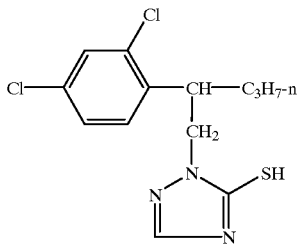

(II-25)

Under an atmosphere of nitrogen and with stirring, a mixture of 1.42 g (5 mmol) of 2-(2,4-dichloro-phenyl)-1-(1,2,4-triazol-1-yl)-pentane, 0.32 g (10 mmol) of sulphur powder and 10 ml of absolute N-methyl-pyrrolidone is heated at 200° C. for 3 hours. The reaction mixture is subsequently concentrated under reduced pressure. The residue that remains is admixed with ethyl acetate and the resulting mixture is extracted repeatedly with saturated aqueous ammonium chloride solution. The organic phase is dried over sodium sulphate and then concentrated under reduced pressure. The resulting crude product (2.1 g) is purified by silica gel chromatography using a mixture of petroleum ether and ethyl acetate=1:1 as eluent. In this manner, 1.5 g (95% of theory) of 2-(2,4-dichloro-phenyl)-1-(5-mercapto-1,2,4-triazol-1-yl)-pentane are obtained in the form of a solid substance of melting point 103° C.

Example 34

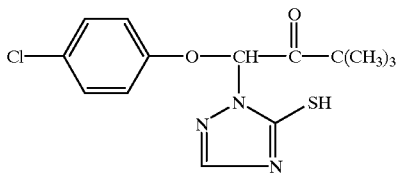

(II-26)

Under an atmosphere of nitrogen and with stirring, a mixture of 2.93 g (10 mmol) of 1-(4-chloro-phenoxy)-1-(1,2,4--triazol-1-yl)-3,3-dimethyl-butan--2-one, 0.64 g (20 mmol) of sulphur powder and 10 ml of absolute N-methylpyrrolidone is heated at 200° C. for 8 hours. The reaction mixture is subsequently concentrated under reduced pressure, and the residue that remains is dissolved in dichloromethane. The resulting mixture is extracted repeatedly with saturated aqueous ammonium chloride solution.

The organic phase is dried over sodium sulphate and then concentrated under reduced pressure. The resulting crude product (2.7 g) is purified by silica gel chromatography using a mixture of petroleum ether and ethyl acetate=1:1 as eluent. In this manner, 2.0 g (62% of theory) of 1-(4-chlorophenoxy)-1-(5-mercapto-1,2,4-triazol-1-yl)-3,3-dimethyl-butan-2-one are obtained in the form of a solid substance of melting point 134 to 136° C.

Example 35

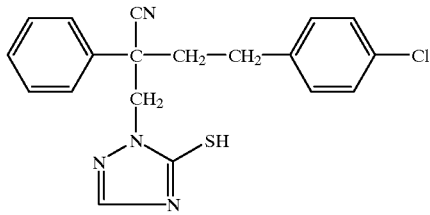

(II-27)

Under an atmosphere of nitrogen and with stirring, a mixture of 1.68 g (5 mmol) of 4-(4-chloro-phenyl)-2-cyano-2-phenyl-1-(1,2,4-triazol-1-yl)-butane, 0.32 g (10 mmol) of sulphur powder and 10 ml of absolute N-methylpyrrolidone is heated at 200° C. for 47 hours. The reaction mixture is subsequently concentrated under reduced pressure, and the residue that remains is dissolved in ethyl acetate. The resulting mixture is extracted repeatedly with saturated aqueous ammonium chloride solution. The organic phase is dried over sodium sulphate and then concentrated under reduced pressure. The resulting crude product (1.9 g) is purified by silica gel chromatography using a mixture of petroleum ether and ethyl acetate=1:1 as eluent. In this manner, 0.7 g (38% of theory) of 4-(4-chloro-phenyl)-2-cyano-2-phenyl-1-(5-mercapto-1,2,4-triazol-1-yl)-butane is obtained in the form of an oil.

$^1$H NMR spectrum (400 MHz; CDCl$_3$, TMS): δ=2.4 (m, 3H); 2.75 (m, 1H); 4.5 (AB, 2H); 7.0 (d, 2H); 7.2 (d, 2H); 7.4 (m, 3H); 7.55 (m, 2H); 7.8 (s, 1H); 11.7 (1H) ppm.

Example A

Erysiphe test (barley)/curative

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *hordei*. 48 hours after the inoculation, the plants are sprayed with the active compound preparation at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, active compound application rates and test results are shown in the table below.

TABLE A

Erysiphe test (barley)/curative

| Active compound | Active compound application rate in g/ha | Efficacy in % |
|---|---|---|
| according to the invention | | |
| (I-1) [2-chlorobenzyl-cyclopropyl-hydroxymethyl-triazole-thiolate sodium salt structure] | 250 | 100 |
| (I-7) [dichlorovinyl-chloromethyl-cyclopropyl-hydroxy-triazole-thiolate diisopropylammonium structure] | 250 | 100 |

Example B
Erysiphe test (barley)/protective

Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, active compound application rates and test results are shown in the table below.

TABLE B

Erysiphe test (barley)/protective

| Active compound | Active compound application rate in g/ha | Efficacy in % |
|---|---|---|
| according to the invention | | |
| 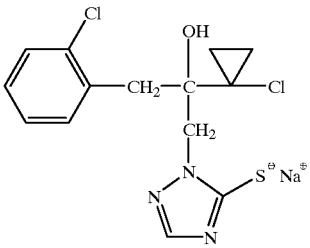<br>(I-1) | 250 | 100 |
| 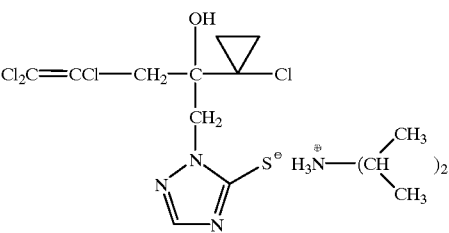<br>(I-7) | 250 | 100 |

Example C

Erysiphe test (wheat)/curative

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration. To test for curative activity, young plants are dusted with spores of *Erysiphe graminis* f.sp. *tritici*. 48 hours after the inoculation, the plants are sprayed with the active compound preparation at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, active compound application rates and test results are shown in the table below.

TABLE C

Erysiphe test (wheat)/curative

| Active compound | Active compound application rate in g/ha | Efficacy in % |
|---|---|---|
| According to the invention | | |
| 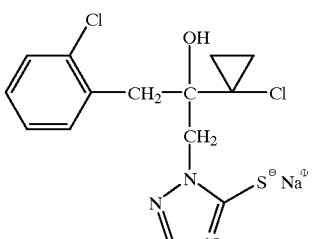<br>(I-1) | 250 | 100 |

TABLE C-continued

Erysiphe test (wheat)/curative

| Active compound | Active compound application rate in g/ha | Efficacy in % |
|---|---|---|
| (I-7) $Cl_2C{=\!=}CCl{-\!\!-}CH_2{-\!\!-}\underset{\underset{\underset{N}{\diagup}\!\!\diagdown\!\!N}{\overset{|}{CH_2}}}{\overset{\overset{OH}{|}}{C}}(\triangleright)\!\!-\!\!Cl \quad N{-\!\!-}S^{\ominus}\ H_3\overset{\oplus}{N}{-\!\!-}(CH(CH_3)_2)_2$ | 250 | 100 |

Example D
Erysiphe test (wheat)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate.

After the spray coating has dried on, the plants are dusted with spores of *Erysiphe graminis* f.sp. *tritici*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, active compound application rates and test results are shown in the table below.

TABLE D

Erysiphe test (wheat)/protective

| Active compound | Active compound application rate in g/ha | Efficacy in % |
|---|---|---|
| According to the invention | | |
| (I-1) 2-Cl-C_6H_4-CH_2-C(OH)(cyclopropyl)(Cl)-CH_2-N(triazole)-S^⊖ Na^⊕ | 250 | 100 |
| (I-7) $Cl_2C{=}CCl{-}CH_2{-}C(OH)(\triangleright)(Cl){-}CH_2{-}N(triazole){-}S^{\ominus}\ H_3\overset{\oplus}{N}{-}(CH(CH_3)_2)_2$ | 250 | 100 |

Example E

Sphaerotheca test (cucumber)/protective

Solvent: 47 parts by weight of acetone

Emulsifier: 3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are dusted with conidia of the fungus *Sphaerotheca fuliginea.*

The plants are subsequently placed in a greenhouse at 23 to 24° C. and a relative atmospheric humidity of approximately 75%.

Evaluation is carried out 10 days after the inoculation. 0% means an efficacy which corresponds to that of the control, whereas an efficacy of 100% means that no infection is observed.

Active compounds, active compound application rates and test results are shown in the table below.

TABLE E

Sphaerotheca test (cucumber)/protective

| Active compound | Active compound application rate in g/ha | Efficacy in % |
|---|---|---|
| According to the invention | | |
| 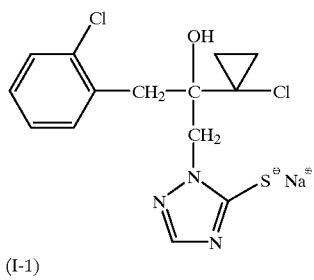<br>(I-1) | 10 | 100 |

Example F

Botrytis test (beans)/protective

Solvent: 47 parts by weight of acetone

Emulsifier: 3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, 2 small pieces of agar overgrown with Botrytis cinerea are placed onto each leaf. The inoculated plants are placed in a dark humid chamber at 20° C.

3 days after the inoculation, the size of the infected areas on the leaves is determined and expressed in %. 0% means an efficacy which corresponds to that of the control, whereas an efficacy of 100% means that no infection is observed.

Active compounds, active compound application rates and test results are shown in the table below.

TABLE F

Botrytis test (beans)/protective

| Active compound | Active compound application rate in g/ha | Efficacy in % |
|---|---|---|
| According to the invention | | |
| (I-1) | 500 | 98 |

Example G

Podosphaera test (apple)/protective

Solvent: 47 parts by weight of acetone

Emulsifier: 3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of the causative organism of apple mildew *Podosphaera leucotricha.* The plants are placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

Active compounds, active compound application rates and test results are shown in the table below.

TABLE G

Podosphaera test (apple)/protective

| Active compound | Active compound application rate in g/ha | Efficacy in % |
|---|---|---|
| According to the invention | | |
| | 50 | 100 |
| (I-2) [2-chlorobenzyl-cyclopropyl-chloromethyl-hydroxy-triazolyl-thiolate] Cu²⁺ salt | | |
| | 50 | 100 |
| (I-4) [2-chlorobenzyl-cyclopropyl-chloromethyl-hydroxy-triazolyl-thiolate] HN(C₄H₉-n)₃ salt | | |

TABLE G-continued

Podosphaera test (apple)/protective

| Active compound | Active compound application rate in g/ha | Efficacy in % |
|---|---|---|
| | 50 | 100 |
| (I-8) [2-chlorobenzyl-cyclopropyl-chloromethyl-hydroxy-triazolyl-thiolate] N(CH₃)₄ salt | | |

Example H

Venturia test (apple)/protective

Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are inoculated with an aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

Active compounds, active compound application rates and test results are shown in the table below.

TABLE H

Venturia test (apple)/protective

| Active compound | Active compound application rate in g/ha | Efficacy in % |
|---|---|---|
| According to the invention | | |
| (I-2) $\left[\text{2-Cl-C}_6\text{H}_4\text{-CH}_2\text{-C(OH)(cyclopropyl-Cl)-CH}_2\text{-(1,2,4-triazol-1-yl-5-S}^{\ominus})\right]_2 \text{Cu}^{2\oplus}$ | 50 | 100 |
| (I-4) 2-Cl-C$_6$H$_4$-CH$_2$-C(OH)(cyclopropyl-Cl)-CH$_2$-(1,2,4-triazol-1-yl-5-S$^{\ominus}$) H$\overset{\oplus}{N}$(C$_4$H$_9$-n)$_3$ | 50 | 100 |
| (I-3) 2-Cl-C$_6$H$_4$-CH$_2$-C(OH)(cyclopropyl-Cl)-CH$_2$-(1,2,4-triazol-1-yl-5-S$^{\ominus}$) H$\overset{\oplus}{N}$(C$_2$H$_5$)$_3$ | 50 | 100 |
| (I-7) Cl$_2$C=CCl-CH$_2$-C(OH)(cyclopropyl-Cl)-CH$_2$-(1,2,4-triazol-1-yl-5-S$^{\ominus}$) H$_3$$\overset{\oplus}{N}$-(CH(CH$_3$)$_2$)$_2$ | 50 | 100 |

We claim:
1. A triazolyl-mercaptide of the formula

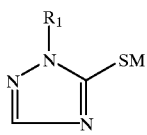
(I)

wherein

M represents a sodium or potassium cation, a stoichiometrically equivalent of a magnesium, calcium, copper, zinc, iron or nickel cation or represents an ammonium cation of the formula

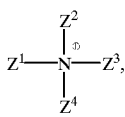

wherein $Z^1$ represents hydrogen or straight-chain or branched alkyl having 1 to 8 carbon atoms, $Z^2$ represents hydrogen or straight-chain or branched alkyl having 1 to 8 carbon atoms, $Z^3$ represents hydrogen, straight-chain or branched alkyl having 1 to 8 carbon atoms, benzyl or phenyl and $Z^4$ represents straight-chain or branched alkyl having 1 to 18 carbon atoms, benzyl or phenyl, and $R^1$ represents a radical of the formula

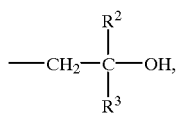

wherein $R^2$ represents straight-chain or branched alkyl having 1 to 6 carbon atoms, where these radicals may be mono- to tetrasubstituted by identical or different substituents selected from the group consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, where each of these radicals may be mono- to trisubstituted by identical or different substituents selected from the group consisting of halogen, alkoxy having 1 to 4 carbon atoms and/or cycloalkyl having 3 to 7 carbon atoms, or represents cycloalkyl having 3 to 7 carbon atoms, where each of these radicals may be mono- to trisubstituted by identical or different substituents selected from the group consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, where each of these radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, and R³ represents straight-chain or branched alkyl having 1 to 6 carbon atoms, where these radicals may be mono- to tetrasubstituted by identical or different substituents selected from the group consisting of halogen, alkoxy having 1 to 4 carbon atoms, alkoximino having 1 to 4 carbon atoms in the alkoxy moiety and /or cycloalkyl having 3 to 7 carbon atoms, or represents straight-chain or branched alkenyl having 2 to 6 carbon atoms, where each of these radicals may be mono- to trisubstituted by identical or different substituents selected from the group consisting of halogen, alkoxy having 1 to 4 carbon atoms and/or cycloalkyl having 3 to 7 carbon atoms, or represents cycloalkyl having 3 to 7 carbon atoms, where each of these radicals may be mono- to trisubstituted by identical or different substituents selected from the group consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, where each of these radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or R¹ furthermore represents a radical of the formula

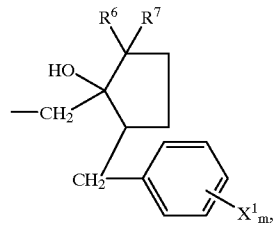

wherein

R⁶ represents hydrogen, methyl, ethyl, n-propyl, isopropyl, n-butyl, isobutyl, sec-butyl, tert-butyl or n-pentyl, R⁷ represents hydrogen, methyl, ethyl, n-propyl, isopropyl, n-butyl, isobutyl, sec-butyl, tert-butyl or n-pentyl, X¹ represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m represents the numbers 0, 1 or 2, where X¹ may represent identical or different radicals if m represents 2, or R¹ furthermore represents a radical of the formula

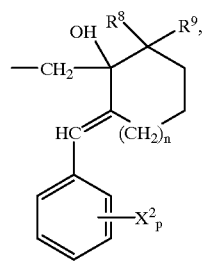

wherein

R[8] represents hydrogen, methyl, ethyl, n-propyl, isopropyl, n-butyl, isobutyl, sec-butyl, tert-butyl or n-pentyl, R[9] represents hydrogen, methyl, ethyl, n-propyl, isopropyl, n-butyl, isobutyl, sec-butyl, tert-butyl or n-pentyl, X[2] represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n represents the numbers 0 or 1 and p represents the numbers 0, 1 or 2, where X[2] may represent identical or different radicals if p represents 2, or R[1] furthermore represents a radical of the formula

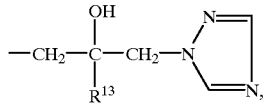

wherein

R[13] represents straight-chain or branched alkyl having 1 to 4 carbon atoms, straight-chain or branched halogenoalkyl having 1 to 4 carbon atoms and 1 to 5 fluorine, chlorine and/or bromine atoms, represents cycloalkyl having 3 to 6 carbon atoms which is optionally mono- to trisubstituted by identical or different substituents selected from the group consisting of fluorine, chlorine, bromine, methyl and/or ethyl, represents phenyl, benzyl or phenethyl, where each of the three last-mentioned radicals may be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or phenoxy which is optionally substituted by halogen and/or alkyl having 1 to 4 carbon atoms, or R[1] furthermore represents a radical of the formula

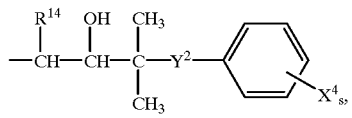

wherein

R[14] represents hydrogen, straight-chain or branched alkyl having 1 to 12 carbon atoms or represents cycloalkyl having 3 to 7 carbon atoms which is optionally mono- to trisubstituted by identical or different substituents selected from the group consisting of halogen and/or alkyl having 1 to 4 carbon atoms, X[4] represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy, s represents the numbers 0, 1, 2 or 3, where X[4] represents identical or different radicals if s represents 2 or 3, and Y[2] represents an oxygen atom, a $CH_2$ group or a direct bond, or R[1] furthermore represents a radical of the formula

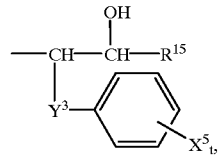

wherein

R[15] represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and/or bromine or represents benzyl which is optionally mono- to trisubstituted by identical or different substituents selected from the group consisting of fluorine, chlorine and/or bromine, X[5] represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl which is optionally mono- to disubstituted by identical or different substituents selected from the group consisting of fluorine, chlorine, bromine and/or methyl or represents phenoxy which is optionally mono- to disubstituted by identical or different substituents selected from the group consisting of fluorine, chlorine, bromine and/or methyl, t represents the numbers 0, 1, 2 or 3, where X[5] represents identical or different radicals if t represents 2 or 3 and Y[3] represents an oxygen atom or represents a $CH_2$ group, or R[1] furthermore represents a radical of the formula

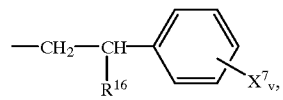

wherein

R[16] represents straight-chain or branched alkyl having 1 to 6 carbon atoms, straight-chain or branched halogenoalkyl having 1 to 6 carbon atoms and 1 to 5 fluorine, chlorine and/or bromine atoms, fluoroalkoxyalkyl having 1 to 3 carbon atoms and 1 to 5 fluorine atoms in the fluoroalkoxy moiety and 1 to 3 carbon atoms in the alkyl moiety, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and/or bromine or represents phenylalkyl having 1 or 2 carbon atoms in the alkyl moiety which is optionally mono- to trisubstituted by identical or different substituents selected from the group consisting of fluorine, chlorine and/or bromine, $X^7$ represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl and v represents the numbers 0, 1, 2 or 3, where $X^7$ represents identical or different radicals if v represents 2 or 3, or $R^1$ furthermore represents a radical of the formula

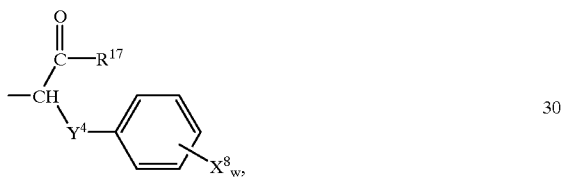

wherein $R^{17}$ represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally mono- to trisubstituted by identical of different substituents selected from the group consisting of fluorine, chlorine and/or bromine or represents benzyl which is optionally mono- to trisubstituted by identical or different substituents selected from the group consisting of fluorine, chlorine and/or bromine, $X^8$ represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl w represents the numbers 0, 1, 2 or 3, where $X^8$ represents identical or different radicals if w represents 2 or 3, and $Y^4$ represents an oxygen atom or represents a $CH_2$ group, or $R^1$ furthermore represents a radical of the formula

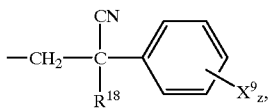

wherein $R^{18}$ represents straight-chain or branched alkyl having 1 to 4 carbon atoms, halogenoalkyl having 1 to 4 carbon atoms and 1 to 5 halogen atoms, phenyl which is optionally mono- to trisubstituted by identical or different substituents selected from the group consisting of halogen, alkyl having 1 to 4 carbon atoms, halogenoalkyl having 1 or 2 carbon atoms having 1 to 5 halogen atoms, alkoxy having 1 to 4 carbon atoms and/or halogenoalkoxy having 1 or 2 carbon atoms and 1 to 5 halogen atoms or represents phenylalkyl having 1 to 4 carbon atoms in the alkyl moiety which is optionally mono- to trisubstituted by identical or different substituents selected from the group consisting of halogen, alkyl having 1 to 4 carbon atoms, halogenoalkyl having 1 or 2 carbon atoms and 1 to 5 halogen atoms, alkoxy having 1 to 4 carbon atoms and/or halogenoalkoxy having 1 or 2 carbon atoms and 1 to 5 halogen atoms, $X^9$ represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and/or methyl or represents phenoxy which is optionally mono- or disubstituted by identical or different substituents selected from the group consisting of fluorine, chlorine, bromine and/or methyl, and z represents the numbers 0, 1, 2 or 3, where $X^9$ represents identical or different radicals if z represents 2 or 3.

2. A process for preparing triazolyl-mercaptides of the formula (I) according to claim 1, comprising reacting a mercapto-triazole of the formula:

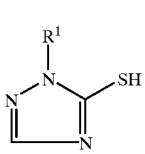

(II)

wherein $R^1$ is as defined in claim 1, either a) with a hydroxide of the formula $M^1$—OH  (III)

wherein $M^1$ represents a sodium or portassium cation, a stoichiometrically equivalent of a magnesium or calcium cation or represents an ammonium cation of the formula

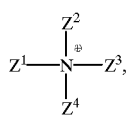

wherein
$Z^1$, $Z^2$, $Z^3$, and $Z^4$ are each as defined in claim 1,
in the presence of a diluent, or
b) with an amine of the formula (IV)

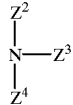

wherein
$Z^2$, $Z^3$, and $Z^4$ are each as defined in claim 1
in the presence of a diluent, or
c) with an acetate of the formula

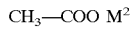   (V)

wherein
$M^2$ represents a stoichiometrically equivalent of a copper, zinc, iron or nickel cation,
in the presence of a diluent.

3. A compound of the formula (I-7)

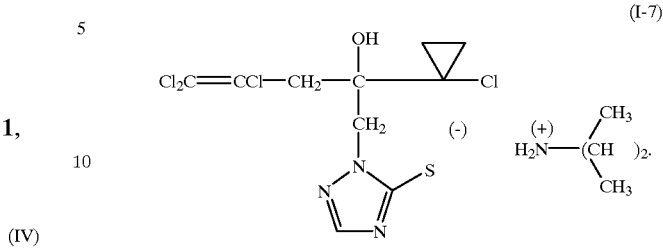

(I-7)

4. A method for controlling undesired microorganisms in plant protection and in the preservation of materials adversely affected by microorganisms, which method comprises applying to such undesired microorganisms or to their habitat a microbicidally effective amount of a triazolyl-mercaptide of the formula as claimed in claim 1.

5. A microbicidal composition comprising a microbicidally effective amount of a triazolyl-mercaptide as claimed in claim 1 and an inert diluent.

* * * * *